United States Patent
Guiles et al.

(10) Patent No.: US 11,369,409 B2
(45) Date of Patent: Jun. 28, 2022

(54) SYSTEM AND METHOD FOR FLUID INGRESS CONTROL FOR A SKIN GRAFTING SYSTEM

(71) Applicant: Medline Industries, Inc., Northfield, IL (US)

(72) Inventors: Marvin A. Guiles, Stow, MA (US); Aaron McPherson, Boston, MA (US); Thomas J. Evans, Bedford, MA (US)

(73) Assignee: Medline Industries, LP, Springfield, IL (US)

( * ) Notice: Subject to any disclaimer, the term of this patent is extended or adjusted under 35 U.S.C. 154(b) by 426 days.

(21) Appl. No.: 16/592,312

(22) Filed: Oct. 3, 2019

(65) Prior Publication Data
US 2021/0100572 A1 Apr. 8, 2021

(51) Int. Cl.
*A61B 17/322* (2006.01)
*A61B 17/00* (2006.01)
*A61M 37/00* (2006.01)

(52) U.S. Cl.
CPC ....... *A61B 17/322* (2013.01); *A61M 37/0015* (2013.01); *A61B 2017/00942* (2013.01); *A61B 2017/00969* (2013.01); *A61B 2017/3225* (2013.01); *A61M 2037/003* (2013.01); *A61M 2205/12* (2013.01)

(58) Field of Classification Search
CPC .......... A61B 17/322; A61B 2017/3225; A61B 2017/00942; A61M 37/0015
See application file for complete search history.

(56) References Cited

U.S. PATENT DOCUMENTS

| | | |
|---|---|---|
| 6,345,553 B1 | 2/2002 | Adler et al. |
| 6,505,530 B2 | 1/2003 | Adler et al. |
| 6,997,923 B2 | 2/2006 | Anderson et al. |
| 9,060,803 B2 | 6/2015 | Anderson et al. |

(Continued)

FOREIGN PATENT DOCUMENTS

WO 2014028626 A1 2/2014

OTHER PUBLICATIONS

Acelity, Cellutome(TM) Epidermal Harvesting System, https://web.archive.org/web/20210528154715/https://www.acelity.com/healthcare-professionals/global-product-catalog/catalog/cellutome-epidermal-harvesting-system, Copyright 3M 2020, 4 pages.

(Continued)

*Primary Examiner* — Katherine H Schwiker
*Assistant Examiner* — Raihan R Khandker
(74) *Attorney, Agent, or Firm* — Quarles & Brady LLP

(57) ABSTRACT

A skin grafting system having a handheld device, a cartridge, and a device shield. The handheld device includes a device housing forming an interior that secures a drive system. The cartridge includes a plurality of hollow microneedles surrounded by a peripheral housing and is configured to be operated by the drive system to extend and retract past the peripheral housing into a subject to harvest tissue during a skin grafting process. The device shield is formed of a polymer extending from an interior opening to an exterior edge, the interior opening sized to extend about the peripheral housing to positon the exterior edge over the device housing to control ingress of fluids into the interior of the device housing from fluid about the peripheral housing of the cartridge during the skin grafting process performed using the skin grafting system.

15 Claims, 13 Drawing Sheets

(56) References Cited

U.S. PATENT DOCUMENTS

| | | | |
|---|---|---|---|
| 9,743,949 B2 | 8/2017 | Guiles et al. | |
| 9,827,006 B2 | 11/2017 | Anderson et al. | |
| 9,895,162 B2 | 2/2018 | Anderson et al. | |
| 2004/0002723 A1* | 1/2004 | Ball | A61F 2/08 606/180 |
| 2005/0137525 A1 | 6/2005 | Wang et al. | |
| 2005/0283141 A1 | 12/2005 | Giovannoli | |
| 2011/0087177 A2 | 4/2011 | Weston | |
| 2011/0319920 A1* | 12/2011 | Kikkawa | A61B 5/150984 606/186 |
| 2012/0271320 A1* | 10/2012 | Hall | A61B 17/322 606/132 |
| 2015/0216545 A1 | 8/2015 | Anderson et al. | |
| 2015/0320990 A1* | 11/2015 | Burton | A61M 5/1454 604/173 |
| 2015/0335319 A1 | 11/2015 | Chin et al. | |
| 2016/0015416 A1 | 1/2016 | Franco et al. | |
| 2016/0121091 A1* | 5/2016 | Burton | A61M 37/0015 604/173 |
| 2016/0310157 A1* | 10/2016 | Guiles | A61B 17/3421 |
| 2018/0000504 A1 | 1/2018 | Knowlton | |
| 2018/0036029 A1 | 2/2018 | Anderson et al. | |
| 2018/0140316 A1 | 5/2018 | Anderson et al. | |
| 2019/0008542 A1 | 1/2019 | Guiles et al. | |
| 2019/0090897 A1 | 3/2019 | Ma | |
| 2021/0100572 A1 | 4/2021 | Guiles et al. | |

OTHER PUBLICATIONS

Bellus Medical, SkinPen Microneedling System, Instructions for Use, https://skinpen.com/wp-content/uploads/2018/03/SkinPen-Instructions-For-Use.pdf, Mar. 21, 2018, 16 pages.

Bellus Medical, SkinPen Microneedling, https://web.archive.org/web/20191204092932/https://skinpen.com/, Copyright 2019 Bellus Medical, 4 pages.

KCI Medical, V.A.C. Therapy Advanced Wound Healing by Design, https://web.archive.org/web/20171015053528/http://www.kci-medical.sg/SG-ENG/vactherapy, Oct. 15, 2017, 1 page.

Renovacare, Inc., SkinGun(TM) and CellMist(TM) Technology Overview, https://web.archive.org/web/20190831012920/https://www.renovacareinc.com/technology/, Copyright 2019 RenovaCare, Inc., 4 pages.

S2medical, Medical. Skin Grafting, Instagraft, . Instagraft, https://web.archive.org/web/20201130053246/https://www.s2m.se/skin-grafting, Nov. 30, 2020, 2 pages.

Smith + Nephew, Versajet II, Hydrosurgery System, https://www.smith-nephew.com/key-products/advanced-wound-management/versajet/, Sep. 9, 2019, 3 pages.

Ultramist, UltraMIST for Wound Healing, https://web.archive.org/web/20190630011405/https://www.ultramist.com/, Copyright 2019 Celularity, Inc., 5 pages.

International Searching Authority. International Search Report and Written Opinion, PCT/US2020/053413, dated Dec. 21, 2020, 7 pages.

\* cited by examiner

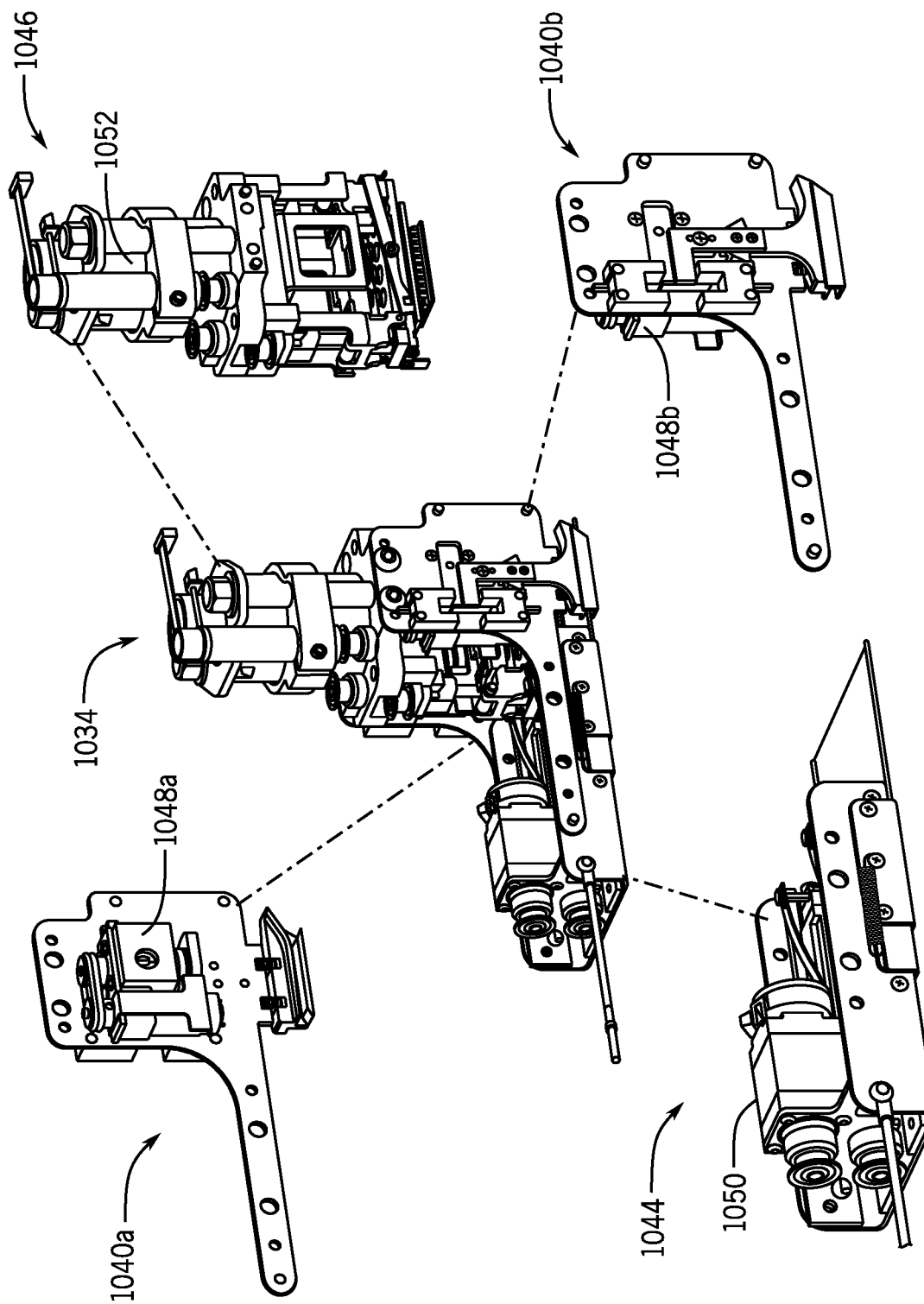

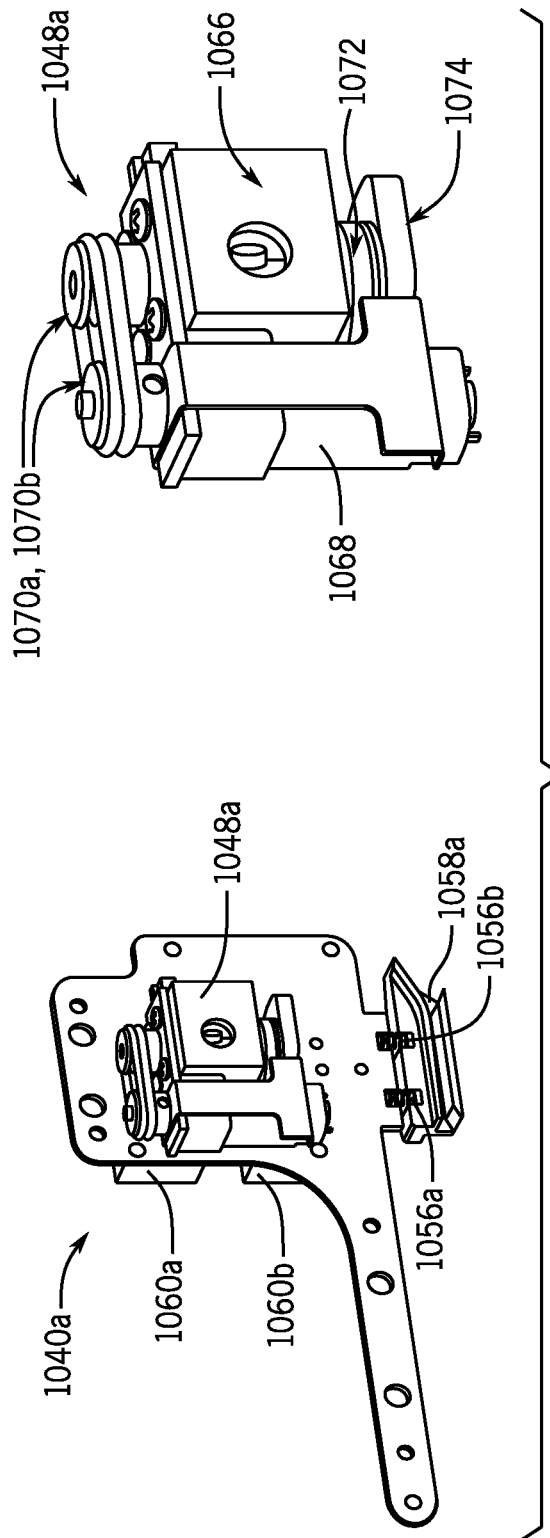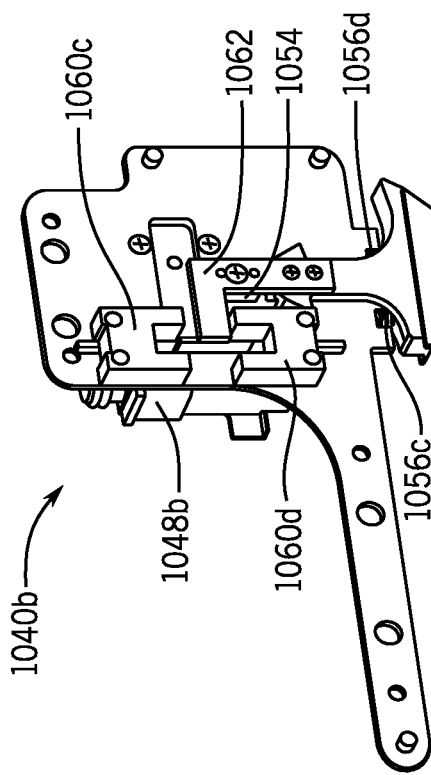
FIG. 4B
FIG. 4C

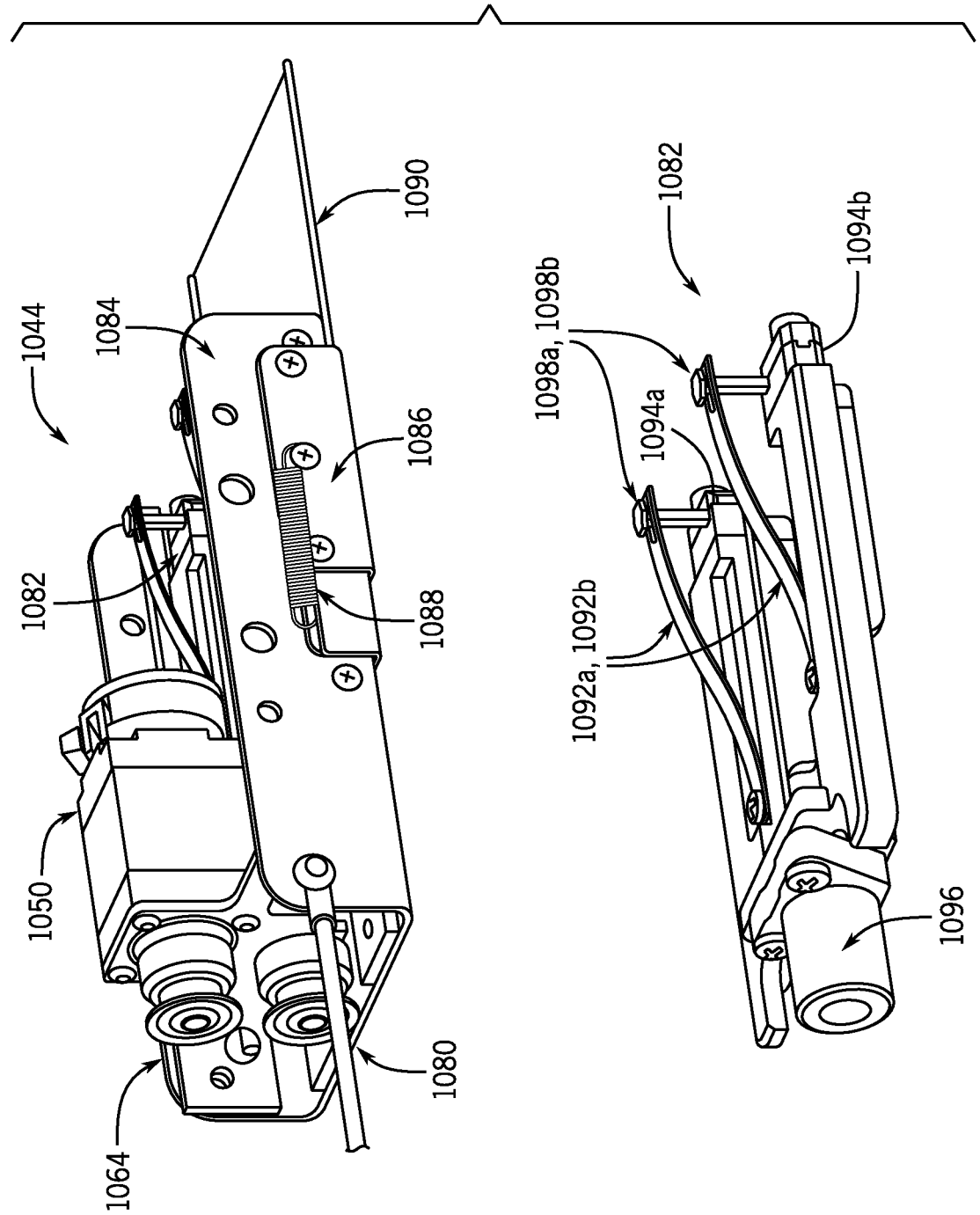

SYSTEM AND METHOD FOR FLUID INGRESS CONTROL FOR A SKIN GRAFTING SYSTEM

BACKGROUND OF THE INVENTION

The subject matter disclosed herein generally relates to a skin grafting system and, more particularly, to a system that may include a device for harvesting and scattering skin microcolumns.

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery and birth defects. Availability of tissue for autografting can be limited by characteristics of candidate donor sites, including a number and/or total area of tissue grafts, healing behavior of the donor site, similarity of the donor and recipient sites, aesthetic considerations, and the like.

Skin grafting can be performed surgically. For example, a conventional autograft procedure may include excision or surgical removal of burn injured tissue, choosing a donor site, which may be an area from which healthy skin is removed to be used as cover for the cleaned burned area, and harvesting, where the graft may be removed from the donor site (e.g., using an instrument similar to an electric shaver). Such instrument (e.g., a dermatome) can be structured to gently shave a thin piece of tissue (e.g., about $^{10}/_{1000}$ of an inch thick for a split-thickness graft) from the skin at the undamaged donor site to use as a skin graft. The skin graft can then be placed over the cleaned wound to heal. Donor skin tissue can be removed to such a depth that the donor site can heal on its own, in a process similar to that of healing of a second degree burn.

Traditionally, sheet grafts and meshed grafts are the two types of autografts often used for a permanent wound coverage. A sheet graft can refer to a piece of skin tissue removed from an undamaged donor site of the body, in a process that may be referred to as harvesting. The size of the donor skin piece that is used may be about the same size as the damaged area. The sheet graft can be applied over the excised wound, and stapled or otherwise fastened in place. The donor skin tissue used in sheet grafts may not stretch significantly, and a sheet graft can be obtained that is slightly larger than the damaged area to be covered because there may often be a slight shrinkage of the graft tissue after harvesting.

Sheet grafts can provide an improved appearance of the repaired tissue site. For example, sheet grafts may be used on large areas of the face, neck and hands if they are damaged, so that these more visible parts of the body can appear less scarred after healing. A sheet graft may be used to cover an entire burned or damaged region of skin. Small areas of a sheet graft can be lost after placement because a buildup of fluid (e.g., a hematoma) can occur under the sheet graft following placement of the sheet graft.

A meshed skin graft can be used to cover larger areas of open wounds that may be difficult to cover using sheet grafts. Meshing of a skin graft can facilitate skin tissue from a donor site to be expanded to cover a larger area. It also can facilitate draining of blood and body fluids from under the skin grafts when they are placed on a wound, which may help prevent graft loss. The expansion ratio (e.g., a ratio of the unstretched graft area to the stretched graft area) of a meshed graft may typically be between about 1:1 to 1:4. For example, donor skin can be meshed at a ratio of about 1:1 or 1:2 ratio, whereas larger expansion ratios may lead to a more fragile graft, scarring of the meshed graft as it heals, and/or extended healing times.

A conventional graft meshing procedure can include running the donor skin tissue through a machine that cuts slits through the tissue, which can facilitate the expansion in a pattern similar to that of fish netting or a chain-link fence. Healing can occur as the spaces between the mesh of the stretched graft, which may be referred to as gaps or interstices, fill in with new epithelial skin growth. However, meshed grafts may be less durable graft than sheet grafts, and a large mesh can lead to permanent scarring after the graft heals.

As an alternative to autografting, skin tissue obtained from recently-deceased people (which may be referred to, e.g. as a homograft, an allograft, or cadaver skin) can be used as a temporary cover for a wound area that has been cleaned. Unmeshed cadaver skin can be put over the excised wound and stapled in place. Post-operatively, the cadaver skin may be covered with a dressing. Wound coverage using cadaveric allograft can then be removed prior to permanent autografting.

A xenograft or heterograft can refer to skin taken from one of a variety of animals, for example, a pig. Heterograft skin tissue can also be used for temporary coverage of an excised wound prior to placement of a more permanent autograft, and may be used because of a limited availability and/or high expense of human skin tissue. In some cases religious, financial, or cultural objections to the use of human cadaver skin may also be factors leading to use of a heterograft. Wound coverage using a xenograft or an allograft is generally a temporary procedure which may be used until harvesting and placement of an autograft is feasible.

Harvesting of the graft tissue from the donor site can generally generate undesirable large-scale tissue damage to the donor site. On the other hand, small areas of skin wounding adjacent to healthy tissue can be well-tolerated, and may heal quickly. Such healing of small wounds can occur in techniques such as "fractional photothermolysis" or "fractional resurfacing," in which patterns of damage having a small dimension can be created in skin tissue. These exemplary techniques are described, for example, in U.S. Pat. No. 6,997,923. Small-scale damage patterns can heal quickly by regrowth of healthy tissue, and can further provide desirable effects such as skin tightening without visible scarring.

The mechanism of tissue grafting presents the opportunity for grafting tools to be exposed to clinical "soil" (e.g., blood, tissue, hair, etc.) from the patient. In split-thickness and full-thickness skin grafting (both of which harvest tissue that extends below the epidermis), localized damage to capillaries and/or blood vessels often leads to bleeding. The degree of bleeding can be influenced by patient factors, such as, for example, anticoagulant medications.

Therefore, it would be advantageous to have further systems and methods to shield reusable clinical tools from clinical soil, without sacrificing functionality of the skin harvesting process.

BRIEF DESCRIPTION OF THE DISCLOSURE

In one aspect, the present disclosure provides a skin grafting system having a handheld device, a cartridge, and a disposable device shield. The handheld device includes a device housing forming an interior that secures a drive system. The cartridge includes a plurality of hollow microneedles surrounded by a peripheral housing and is configured to be operated by the drive system to extend and retract past the peripheral housing into a subject to harvest tissue during a skin grafting process. The device shield is formed of a polymer extending from an interior opening to an exterior edge, the interior opening sized to extend about the peripheral housing to positon the exterior edge over the device housing to inhibit ingress of fluids into the interior of the device housing from fluid about the peripheral housing of the cartridge during the skin grafting process performed using the skin grafting system.

In another aspect, the present disclosure provides a skin grafting system having a handheld device, a cartridge, and a device shield. The handheld device includes a device housing having an engagement slot formed therein and creating an interior that secures a drive system. The cartridge is removably engaged with the handheld device through the engagement slot and includes a plurality of hollow microneedles surrounded by a peripheral housing and configured to be operated by the drive system to extend and retract past the peripheral housing into a subject to harvest tissue during a skin grafting process. The device shield is formed of a flexible membrane extending from an interior opening to an exterior edge, the interior opening sized to extend about and be moved along the peripheral housing to form a barrier over the engagement slot when the exterior edge is arranged to extend over the device housing.

The following description and the accompanying drawings set forth in detail certain illustrative embodiments of the present disclosure. However, these embodiments are indicative of but a few of the various ways in which the principles of the disclosure can be employed. Other embodiments and features will become apparent from the following detailed description of the present disclosure when considered in conjunction with the drawings.

BRIEF DESCRIPTION OF THE DRAWINGS

The descriptions hereafter are provided with reference to the accompanying drawings, wherein like reference numerals denote like elements.

FIG. 4A is a rear perspective view of an internal drive assembly and related elements corresponding to the handheld device of FIG. 2A, in accordance with some implementations of the present disclosure.

FIG. 4B is a right perspective view of a left frame assembly corresponding to the internal assembly of FIG. 4A, in accordance with some implementations of the present disclosure.

FIG. 4C is a right perspective view of a right frame assembly corresponding to the internal assembly of FIG. 4A, in accordance with some implementations of the present disclosure.

FIG. 4D is a rear perspective view of a horizontal component assembly corresponding to the internal assembly of FIG. 4A, in accordance with some implementations of the present disclosure.

DETAILED DESCRIPTION OF THE DISCLOSURE

Figure 1:
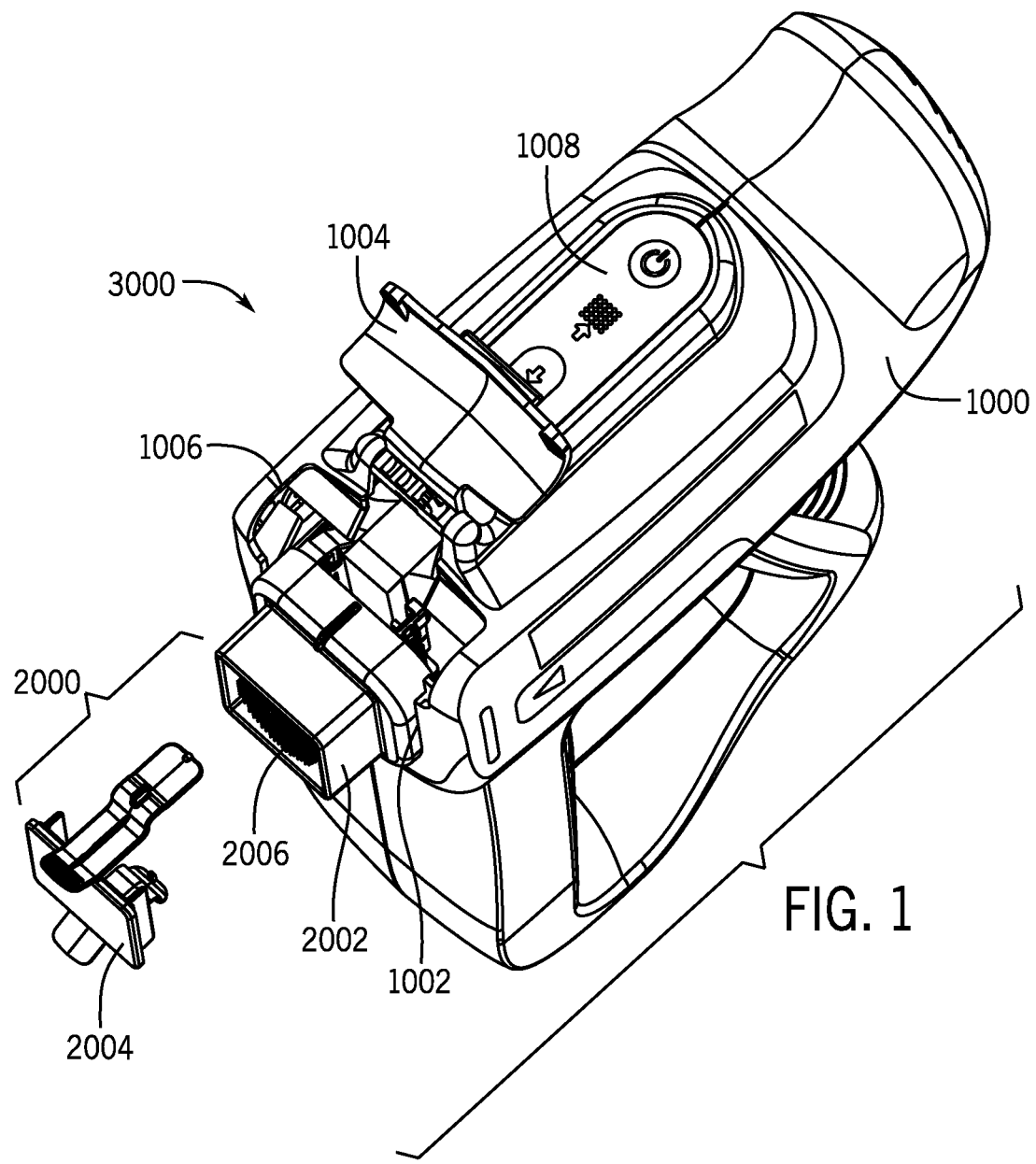
FIG. 1 is a top perspective view of a skin grafting system, including a cartridge, in accordance with some implementations of the present disclosure.

The following discussion is presented to enable a person skilled in the art to make and use the systems and methods of the present disclosure. Various modifications to the illustrated embodiments will be readily apparent to those skilled in the art, and the high-level principles herein can be applied to other embodiments and applications without departing from embodiments of the present disclosure. Thus, embodiments of the present disclosure are not intended to be limited to embodiments shown, but are to be accorded the widest scope consistent with the principles and features disclosed herein.

The detailed description is to be read with reference to the figures. The figures depict selected embodiments and are not intended to limit the scope of embodiments of the present disclosure. Skilled artisans will recognize the examples provided herein have many useful alternatives and fall within the scope of embodiments of the present disclosure. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. As used herein, unless expressly stated otherwise, "connected" means that one element/feature is directly or indirectly connected to another element/feature, and not necessarily electrically or mechanically. Likewise, unless expressly stated otherwise, "coupled" means that one element/feature is directly or indirectly coupled to another element/feature, and not necessarily electrically or mechanically.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., digital signal processing elements, logic elements, diodes, etc., which may carry out a variety of functions under the control of one or more processors or other control devices. Other embodiments may employ program code, or code in combination with other circuit components.

As described above, the present disclosure generally relates to a skin grafting system and, more particularly, to a system that may include a device for harvesting and scattering skin microcolumns. In some situations, the process of harvesting the skin microcolumns can include penetrating donor site tissue. Although generally minimal, harvesting the microcolumns often causes localized bleeding. Blood quantity from the donor site can depend on a variety of factors, such as, for example, number of tissue punctures/penetrations, number of harvesting processes conducted on a single tissue area, number of harvesting processes conducted with a single cartridge (as described below), patient blood pressure, platelet count, medication, donor site treatments, and/or comorbidities. In some situations, it may be advantageous to prevent blood contact and/or ingress into portions of the skin grafting system. In particular, it may be advantageous to prevent blood ingress to reusable elements of the skin grafting system.

As an example, healthcare facilities often have standard cleaning, disinfecting, and/or sterilization procedures that must be performed when an instrument is reusable between patients. Specifically, to minimize the risk of spread of infection, all blood and body substances should be treated as potentially infectious. With complex instruments, blood ingress into an instrument housing can result in procedure delays, lengthy sterilization processes, and/or instrument replacement (and associated cost), among other things. Accordingly, the present disclosure includes systems for preventing blood ingress into a handheld device (e.g., a reusable handheld device) corresponding to a skin grafting system.

Referring now to FIG. 1, a skin grafting system 3000 is shown, in accordance with some implementations of the present disclosure. In some configurations, the skin grafting system 3000 can be configured to harvest and scatter donor tissue. As shown, the skin grafting system 3000 can include a handheld device 1000 (which can be reusable) and a cartridge assembly 2000. As will be described in greater detail below, the cartridge assembly 2000 can include a cartridge 2002 and a cartridge cover 2004. The cartridge 2002 can include a microneedle and pin array 2006, according to some configurations. Notably, the cartridge 2002 can include a simplified microneedle array 2006 (i.e., without pins).

Figure 2B:
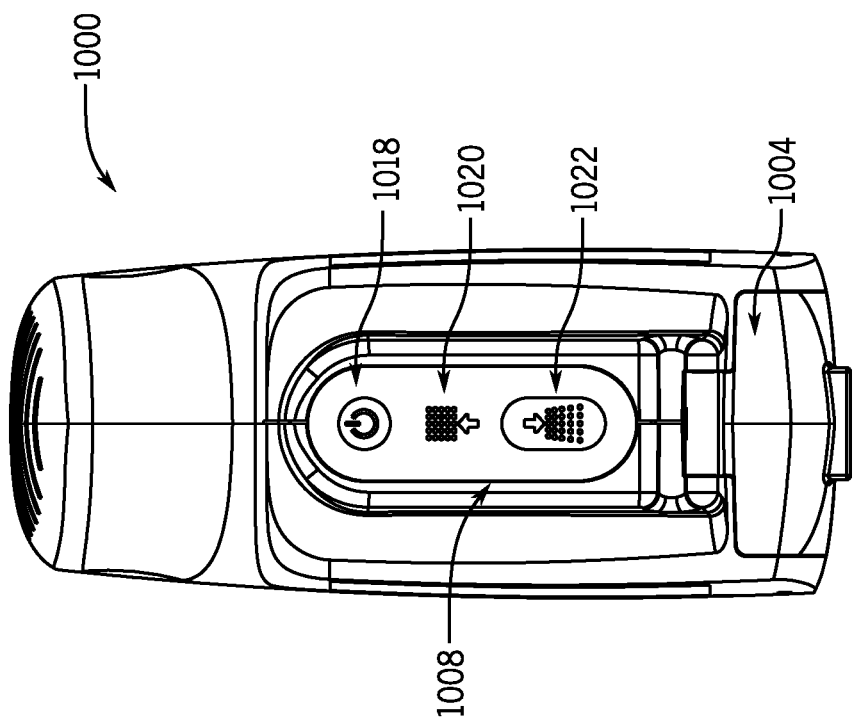
FIG. 2B is a top view of a user interface that may be included in the system of FIG. 2A, in accordance with some implementations of the present disclosure.
Figure 2A:
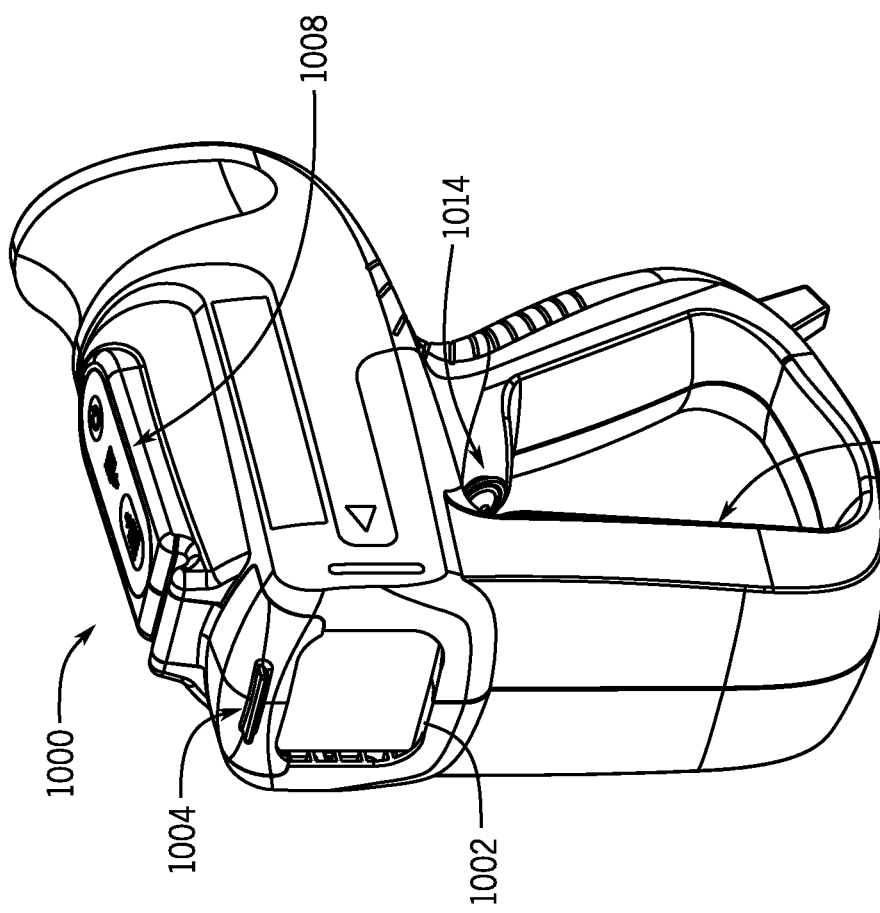
FIG. 2A is a front perspective view of the system of FIG. 1.

As shown by FIGS. 1-2B, the handheld device 1000 can include an engagement slot 1002 configured to receive the cartridge assembly 2000. A loading door 1004 can move between an "open" position (see, e.g., FIG. 1) and a "closed" position (see, e.g., FIGS. 2A-2B). In some configurations, the loading door 1004 can be hinged and further configured to open and close over a loading aperture 1006. The handheld device 1000 can include a door sensor, which can determine the position of the loading door 1004. The loading aperture 1006 can be sized such that the cartridge assembly 2000 can slide in and out of the engagement slot 1002, as desired by the user. Advantageously, the cartridge assembly 2000 can be single-use and/or disposable (including, for example, multiple uses for a single patient), while the handheld device 1000 can be designed to be multi-use. As shown by FIG. 2A, the handheld device 1000 can further include a trigger 1014. The trigger 1014 can be configured to activate a harvesting process and/or a scattering process in response to selection via a user interface 1008 and/or trigger inputs by a user. In some configurations, the handheld device 1000 can include an indicator light 1016. The indicator light 1016 can be positioned such that a user can readily view the indicator light 1016 during harvesting and/or scattering.

In some configurations, the handheld device 1000 can include a user interface 1008. As shown, the user interface 1008 can include a stand-by input 1018, an indicator light 1020, and/or a scatter input 1022. In some configurations, the indicator light 1020 can operate the same as, or similar to, the indicator light 1016 (as described above). The stand-by input 1018, the indicator lights 1016, 1020, and the scatter input 1022 can provide visual feedback to a user that correspond to current operation of the skin grafting system 3000 as the skin grafting system 3000 is utilized according to a skin grafting process, such as will be described.

Figure 3A:
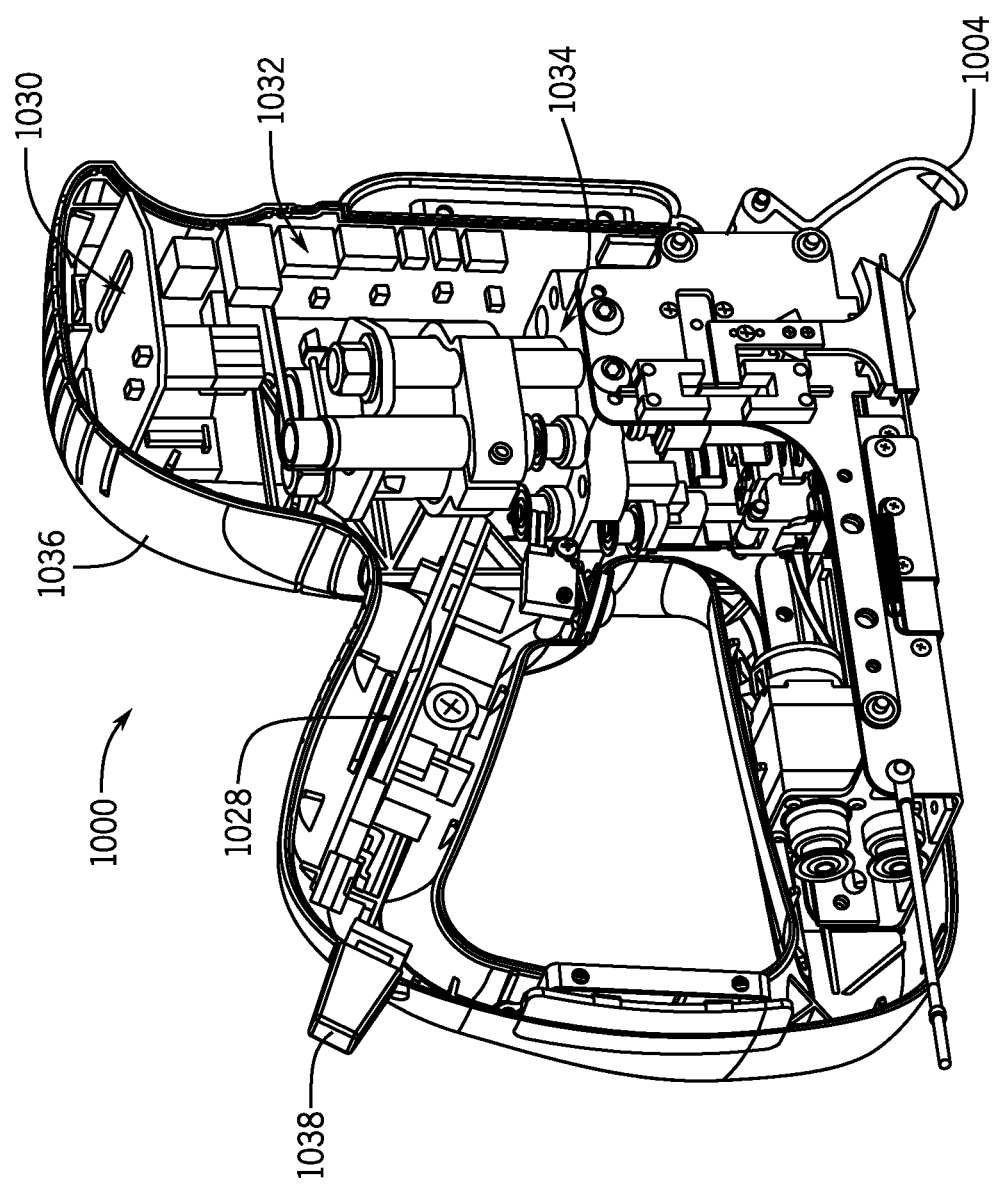
FIG. 3A is a cutaway view of the handheld device of FIG. 2A, in accordance with some implementations of the present disclosure.
Figure 3B:
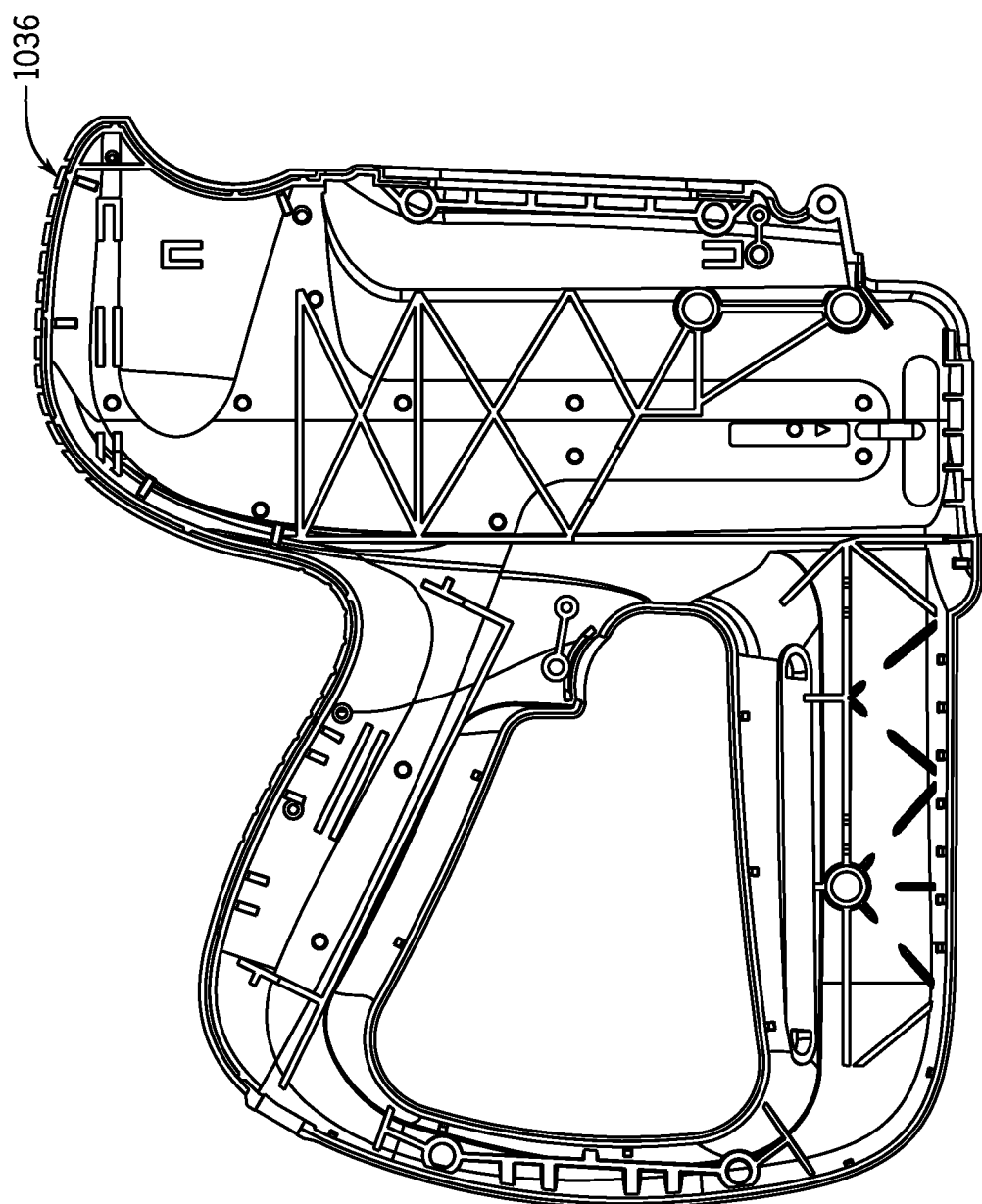
FIG. 3B is a cutaway view of a housing corresponding to the handheld device of FIG. 2A, in accordance with some implementations of the present disclosure.

Referring now to FIGS. 3A-3B, cutaway views of the handheld device 1000 are shown, according to configurations of the present disclosure. The handheld device 1000 is shown to include various internal controllers. In some configurations, the handheld device 1000 can include a power module 1028, a solenoid controller 1030, and/or a main controller 1032. The power module 1028 can be in electrical communication with a power input 1038. In some configurations, a drive system can include a solenoid in communication with the solenoid controller 1030.

Still referring to FIGS. 3A-3B, in some configurations, the handheld device 1000 can include a housing 1036. The housing 1036 can include a left enclosure half and a right enclosure half. In some configurations, each of the left enclosure half, the right enclosure half, the loading door 1004 and the enclosure mount cover can be individually injection molded. The left and right enclosure halves can be made up of a hard plastic substrate, and in some configurations, a softer elastomeric over-molded section. Similarly, the loading door 1004 and the enclosure mount cover can be made up of hard plastic substrate. In some configurations, the interior of the housing 1036 can interface with internal subassemblies. As an example, ribs can be affixed to the interior of the housing 1036, and can be configured to support various printed circuit boards (PCBs). The ribs can separate the PCBs (e.g., power module 1028, solenoid controller 1030, and main controller 1032) from internal moving components. Additionally, in some configurations, the housing 1036 can support the internal subassembly 1034 via pins and vibration damping boots. This can dampen the operational impacts of the internal subassembly 1034 (e.g., from a user, from internal moving components), as well as protect the internal subassembly 1034 from damage due to external impacts (e.g., from dropping the handheld device 1000.

Figure 4E:
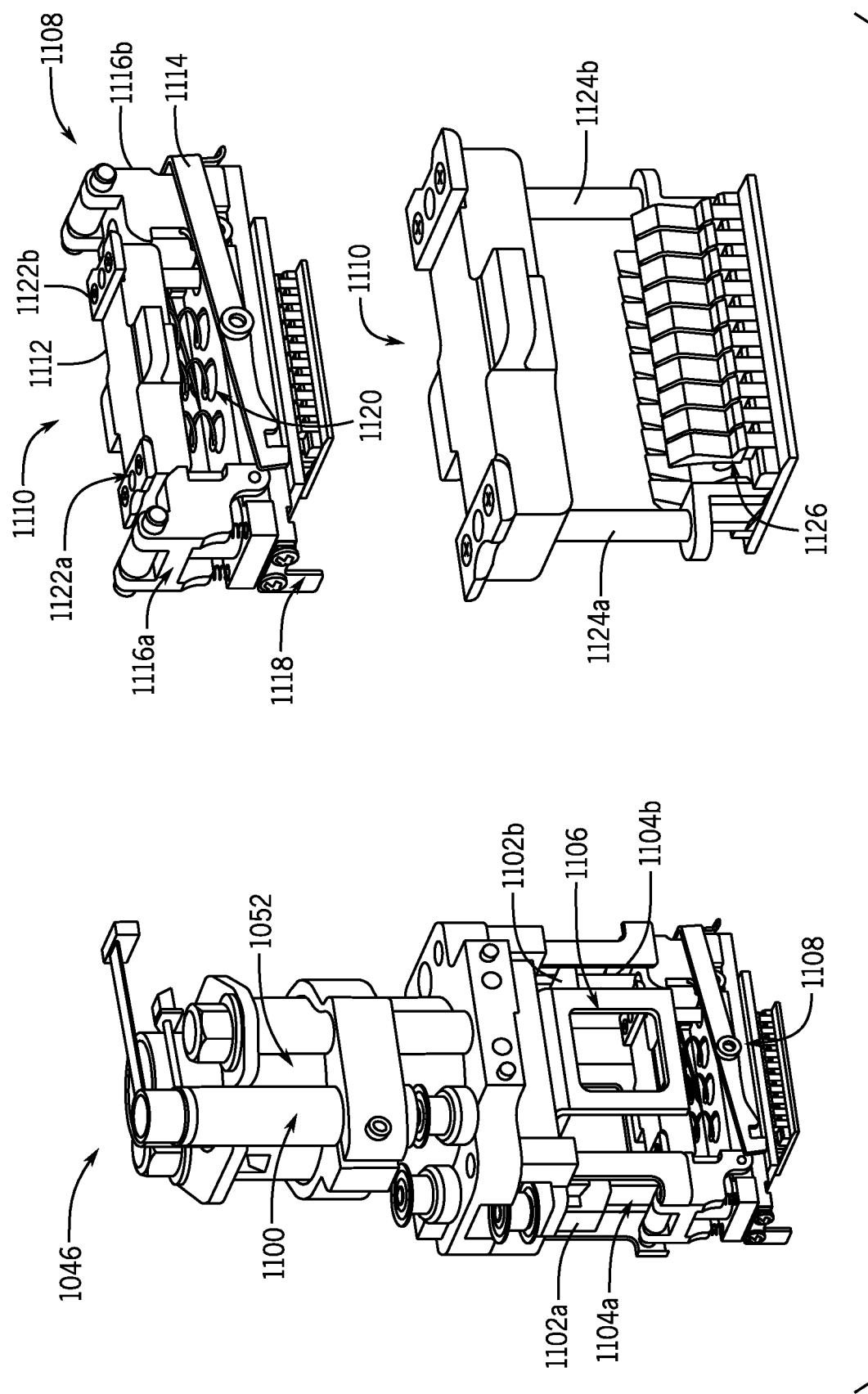
FIG. 4E is a rear perspective view of a vertical component assembly corresponding to the internal assembly of FIG. 4A, in accordance with some implementations of the present disclosure.

Referring now to FIGS. 4A-4E, various internal assemblies corresponding to handheld device 1000 are shown, according to some configurations. FIG. 4A shows the internal subassembly 1034 that can include a left frame assembly 1040a, a right frame assembly 1040b, a horizontal component assembly 1044, and/or a vertical component assembly 1046. Each of the left and right frame assemblies 1040a, 1040b can include a corresponding flipper assembly (e.g., left flipper assembly 1048a, right flipper assembly 1048b). In some configurations, the horizontal component assembly 1044 can include a horizontal motor 1050. Further, the vertical component assembly 1046 can include a solenoid 1052.

Still referring to FIGS. 4A-4E, and in particular FIGS. 4B-4C, further exemplary details of the left and right frame assemblies 1040a, 1040b are shown, according to some configurations. In some configurations, the left frame assembly 1040a and the right frame assembly 1040b can be the same or substantially similar (e.g., symmetrical). As shown, the left frame assembly 1040a can include a left flipper assembly 1048a affixed to a first side of a left frame. Additionally, the left frame assembly 1040a can include flag sensors 1060a, 1060b, affixed to a second side of the left frame. The flag sensors 1060a, 1060b can communicate with a position sensing linear slide 1054, and a position sensing flag 1062. In some configurations, the left frame assembly 1040a can include position sensing springs 1056a, 1056b, which can contact a tissue interface 1058a. The tissue interface 1058a can be positioned on a third side of the left frame. In some configurations, the left frame assembly 1040a can attach to a portion of the vertical component assembly 1046 via screws and alignment pins, or other attachment systems.

In some configurations, the right frame assembly 1040b can include flag sensors 1060c, 1060d, affixed to a first side of a right frame. The flag sensors 1060c, 1060d can communicate with a position sensing linear slide 1054, and a position sensing flag 1062. Additionally, as shown, the right frame assembly 1040b can include a right flipper assembly 1048b affixed to a second side of the right frame. In some configurations, the right frame assembly 1040b can include position sensing springs 1056c, 1056d, which can contact a tissue interface 1058b. The tissue interface 1058b can be positioned on a third side of the right frame. In some configurations, the right frame assembly 1040b can attach to a portion of the vertical component assembly 1046 via screws and alignment pins.

The flipper assemblies 1048a, 1048b can include a flipper mounting block 1066, and a flipper motor 1068. In some configurations, the flipper mounting block 1066 can be constructed from a dielectric material. The flipper motor 1068 can be connected to (and control) flipper driver pulleys 1070a, 1070b. A bearing (e.g., a thrust bearing) 1072 can support an axial load exerted by the needle top plate (e.g., needle top plate 1112 as described below) on a flipper 1074. The flipper 1074 can rotate in accordance with motor actuation, and the flipper driver pulleys 1070a, 1070b can prevent any downward movement of the flipper 1074 during operation of the handheld device 1000. In some configurations, the flipper 1074 can include two connected components, such as two brass components that are brazed together. The primary function of the flipper 1074 can be to hold a needle top plate 1112 of FIG. 4E in place when loading needle retract springs. The flipper 1074 can then move out of the way of the needle top plate 1112 during the remainder of normal operation. In some configurations, the flipper mounting block 1066 can act as a guide for solenoid plunger bar 1106 of FIG. 4E (e.g., to keep proper alignment).

Still referring to FIGS. 4A-4E, and in particular FIG. 4D, further exemplary details of the horizontal component assembly 1044 are shown, according to some configurations. The horizontal component assembly can include sensors, actuators, and/or guides for positioning a horizontal carriage assembly 1082 and, thereby, the hammers 1098a, 1098b used to drive microneedles into the tissue (as will be described below). In some configurations, a horizontal flag sensor 1064 can be used to position the horizontal component assembly 1082. As shown, the horizontal component assembly 1044 can include the horizontal carriage assembly 1082 that can be configured to mount the horizontal motor 1050. In some configurations, a horizontal chassis 1084 can support the horizontal carriage assembly 1082. Additionally, the right frame assembly 1040b and the left frame assembly 1040a can be affixed to opposing sides of the horizontal chassis 1084, for example, using rivets. An earth-ground connection 1080 can be attached to the horizontal chassis 1084, according to some configurations.

In some configurations, the horizontal component assembly 1044 can further include a retractable slide door 1090. The slide door 1090 can extend across the loading aperture 1006 when the cartridge 2002 has not been inserted into the engagement slot 1002. Accordingly, a user can be prevented from placing anything into the handheld device 1000 during the absence of the cartridge 2002. The sliding door 1090 can be secured to a sliding door mount 1086, which can be affixed to the horizontal chassis 1084. Additionally, a sliding door spring 1088 can be secured to the sliding door mount 1086, and biased such that the slide door 1090 remains in a "closed" position (i.e., extended across the loading aperture 1006) when a cartridge is not loaded.

As shown, the horizontal carriage assembly 1082 can include hammers 1098a, 1098b, corresponding hammer return springs 1092a, 1092b, and corresponding hammer guides 1094a, 1094b, according to some configurations. Generally, the horizontal carriage assembly 1082 can be configured to position and guide the hammers 1098a, 1098b to drive the microneedles into the tissue. In some configurations, the hammer guides 1094a, 1094b can be made of bronze, which can help to maintain bearing surfaces throughout many harvesting and scattering cycles. Additionally, in some configurations, the hammers 1098a, 1098b can be hardened 17-4 stainless steel, which can provide superior wear characteristics while maintaining anti-corrosion properties. Alternatively, the hammers 1098a, 1098b can be a different bearing material. The horizontal carriage assembly 1082 can further include a horizontal leadscrew drive nut 1096. Additionally, the horizontal leadscrew assembly 1096 can be a Teflon-coated lead screw, and an Acetal drive nut designed to reduce friction. Alternatively, the horizontal leadscrew assembly 1096 can include other material types. The horizontal leadscrew assembly 1096 can provide a pitch adequate for positional resolution and linear force. The horizontal carriage assembly 1082 can additionally use motor stalling to sense whether or not a cartridge is loaded, or if there is a device jam.

Still referring to FIGS. 4A-4E, and in particular FIG. 4E, further exemplary details of the vertical component assembly 1046 are shown, according to some configurations. As shown, the vertical component assembly 1046 can include the solenoid 1052 and corresponding solenoid plunger bar 1106. Additionally, the vertical component assembly 1046 can include a vertical motor 1100, and associated unlock cams 1102a, 1102b and vertical leadscrews 1104a, 1104b. In some configurations, the vertical position of the vertical carriage subassembly 1108 can be controlled by traveling up and down on the vertical leadscrews 1104a, 1104b (e.g., using the vertical motor 1100). As will be described, vertical positioning can move each of the microneedles corresponding to the cartridge 2002. In general, the vertical component assembly 1046 can be configured to interface with and manipulate the cartridge 2002 and its associated components during harvesting and/or scattering of tissue. In some configurations, the vertical motor 1100 can be sized to fit within the vertical component assembly 1046 while still providing the torque and speeds necessary for manipulating the microneedle positions.

In some configurations, the solenoid 1052 can deliver an operating force to the hammers 1098a, 1098b during harvesting. The solenoid 1052 can be activated by a half wave of AC current, as one non-limiting example. The force delivered by the solenoid 1052 can increase sharply, towards the end of its stroke. In some configurations, the mass of the solenoid plunger bar 1106 and the solenoid plunger can be selected based on the energy needed to drive the microneedles into the tissue. In some configurations, a stop (e.g., a brass stop) can be integrated into the solenoid 1052, which can enable extension control of the solenoid plunger bar 1106 and absorption of remaining kinetic energy at the end of the stroke.

In some configurations, the vertical component assembly 1046 can include a vertical carriage assembly 1108. As shown, the vertical carriage assembly 1108 can include a needle retract slide 1110 with a top plate 1112. In some configurations, opposite ends of the vertical carriage assembly 1108 can include needle retract slide-latches 1116a, 1116b with corresponding latch plates 1122a, 1122b. The latch plates 1122a, 1122b can define a maximum position of the needle retract slide 1110. Additionally, needle retract springs 1120 can be integrated into the vertical carriage assembly 1108, such that efficient retraction of the microneedles can be achieved over the pins. The needle retract slide-latches 1116a, 1116b can be used to lock down the needle retract slide 1110 in preparation for harvesting. The vertical carriage assembly 1108 can also move both the needles and pins (e.g., pins within the microneedles) at the same time.

In some configurations, the vertical carriage assembly 1108 can include a cartridge latch 1114, which can be configured to secure the cartridge 2002 upon insertion into the loading aperture 1006. Additionally, a vertical flag 1118 can be affixed to the exterior of the vertical carriage assembly 1108, according to some configurations. As shown, the needle retract slide 1110 can further include guideposts 1124a, 1124b, which can be configured to guide the needle retract slide 1110 during vertical movement. In some configurations, the needle retract slide 1110 can include lockdown latches 1126, which can be in contact with the guideposts 1124a, 1124b, and configured to engage and disengage the microneedles during operating of the handheld device 1000. The needle retract slide 1110 can be a spring loaded subassembly that serves at least two purposes. First, the slide 1110 can lock needle modules down (after being driven into the tissue). Second, the slide 1110 can retract the needles. In some configurations, the needle retract slide 1110 is only capable of retracting the needles, and cannot move the needles forward. Additionally, in some configurations, the lockdown latches 1126 may be only functional after the skin grafting system 3000 has gone through initialization. Further detail regarding the operation of the skin grafting system 3000 is provided below.

Figure 5A:
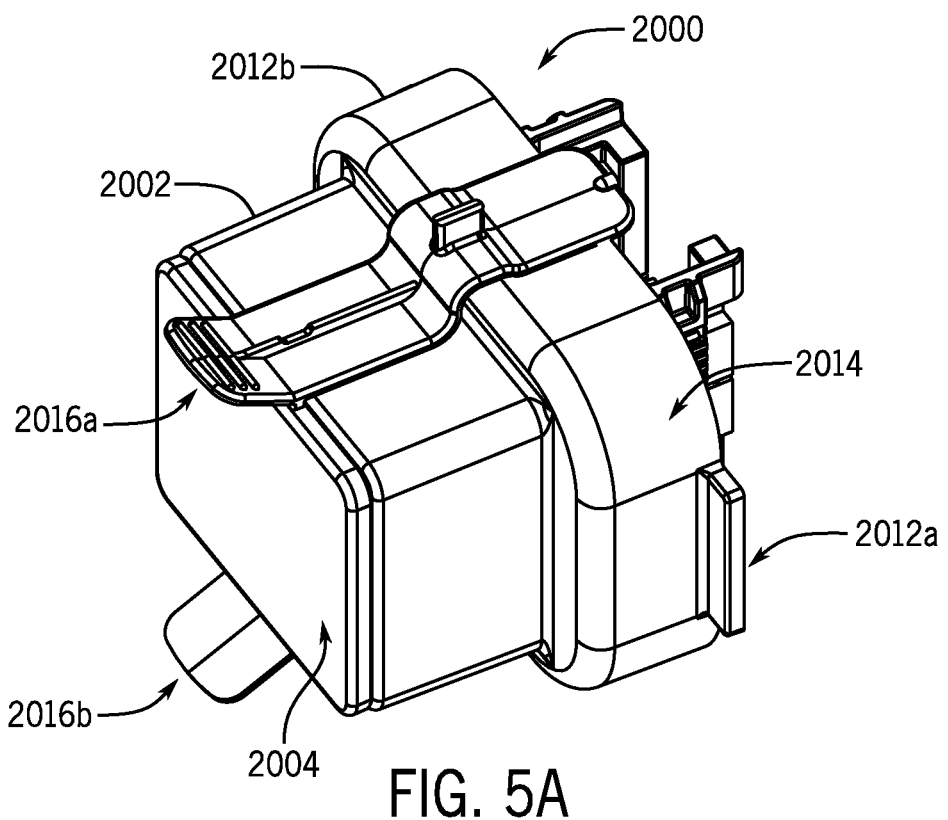
FIG. 5A is a perspective view of a cartridge assembly including a removable cover, in accordance with some implementations of the present disclosure.
Figure 5B:
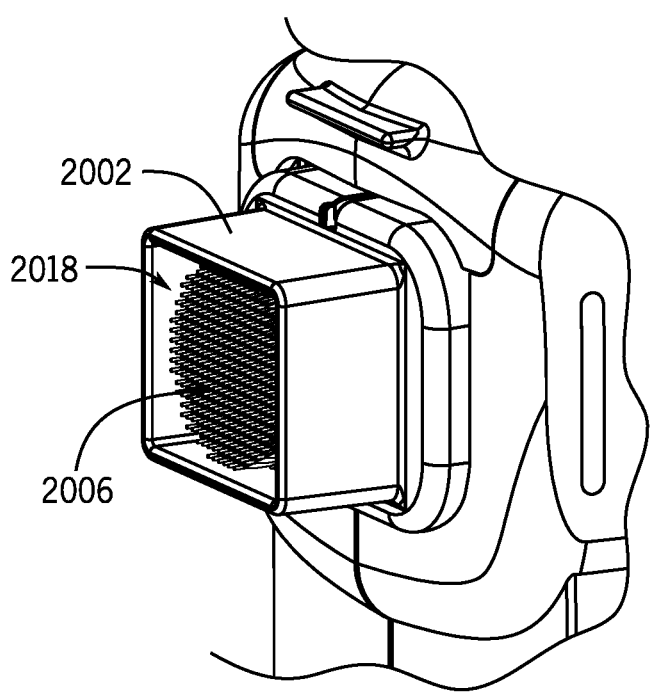
FIG. 5B is a perspective view of a cartridge corresponding to the cartridge of FIG. 5A, in accordance with some implementations of the present disclosure.

Referring now to FIGS. 5A-5B, the cartridge 2002 and a cartridge assembly 2000 are shown, according to some configurations. As shown, the cartridge assembly 2000 can include the cartridge 2002, and a cartridge cover 2004 that can be removably affixed to a microneedle chamber 2018. The microneedle chamber 2018 can enclose a plurality of microneedles 2006. In some configurations, the microneedles 2006 can be arranged as an array within the microneedle chamber 2018. As shown by FIG. 5A, the combination of the cartridge cover 2004 and the microneedle chamber 2018 can form an enclosure for the microneedles 2006. The cartridge cover 2004 can include release levers 2016a, 2016b, which can be simultaneously depressed by a user to remove the cartridge cover 2004 from the cartridge 2002.

In some configurations, the cartridge 2002 can include a tissue stabilizer 2014, which forms a peripheral housing and can be configured to stabilize tissue during harvesting. That is, the tissue stabilizer 2014 forms a peripheral housing that is wider than the microneedle chamber 2018, allowing for a greater distribution of force during use of the skin grafting system 3000 on tissue. As shown, the tissue stabilizer 2014 can further include loading tabs 2012a, 2012b that extend outwardly. In some configurations, the loading tabs 2012a, 2012b can slide into contact with the engagement slot 1002 during loading of the cartridge assembly 2000 into the loading aperture 1006.

Figure 6A:
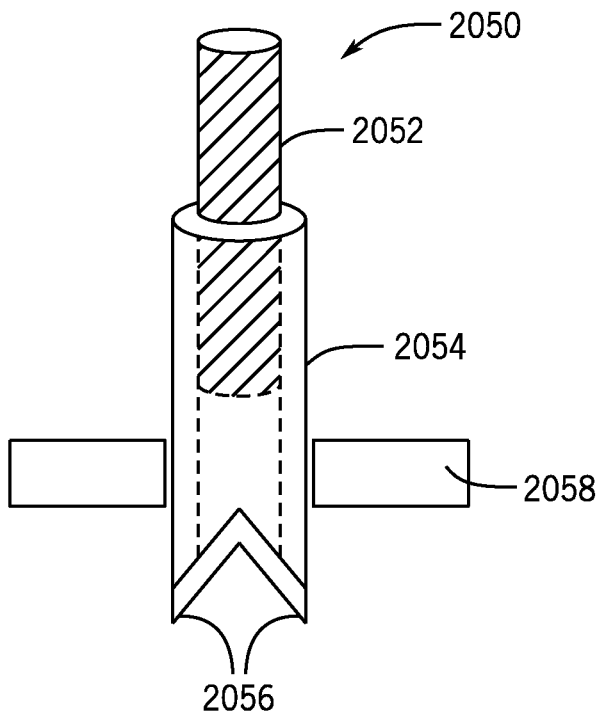
FIG. 6A is an example of a microneedle and pin assembly that can harvest tissue, in accordance with some implementations of the present disclosure.
Figure 6B:
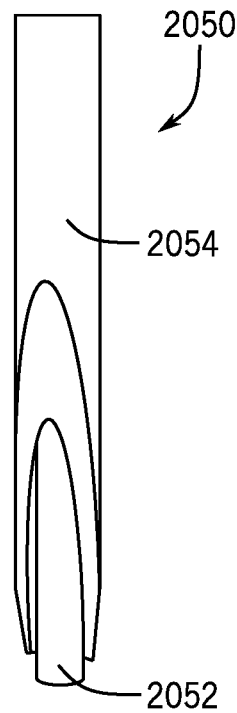
FIG. 6B is a perspective view of a microneedle and pin assembly that can harvest tissue, in accordance with some implementations of the present disclosure.
Figure 6C:
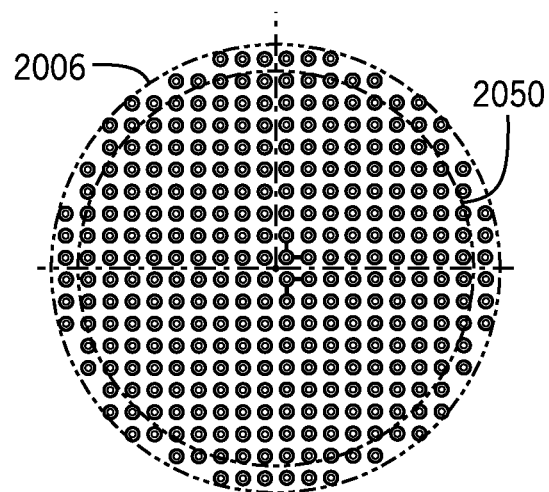
FIG. 6C is a plan view of a microneedle array, in accordance with some implementations of the present disclosure.

Referring now to FIGS. 6A-6C, a microneedle 2050 and a microneedle array 2006 are shown, according to configurations of the present disclosure. The microneedle 2050 can facilitate harvesting of tissue from a donor site. In some configurations, the microneedle 2050 can include a hollow tube 2054 that can include a plurality of points 2056 at the distal end thereof. In some non-limiting examples, needle systems such as described in U.S. Pat. Nos. 9,060,803; 9,827,006; 9,895,162; and US Patent Application Publication Nos. 2015/0216545; 2016/0015416; 2018/0036029; 2018/0140316 and/or combinations or components thereof may be used.

In some configurations of the present disclosure, the hollow tube 2054 can be provided with two points 2056, and the points 2056 can be sufficiently angled for penetrating and cutting the biological tissue to remove small micrografts therefrom. Such a hollow tube 2054 can be provided with two points 2056, and a "narrow heel" portion positioned between the two points 2056. According to some embodiments, the narrow heel portion can be sharpened, such that a cutting edge corresponding to the hollow tube 2054 is created.

In some configurations, the hollow tube 2054 can be slideably attached to a substrate 2058, such that the hollow tube 2054 can pass through a hole provided in the substrate 2058, as shown in FIG. 6A. The position of the hollow tube 2054 relative to the substrate 2058 can be controlled by translating the hollow tube 2054 relative to the substrate 2058, e.g., substantially along the longitudinal axis of the hollow tube 2054. In this manner, the distance that the distal end of the hollow tube 2054 protrudes past the lower surface of the substrate 2058 can be controllably varied.

The microneedle 2050 can further include a pin 2052 provided in the central lumen or opening of the hollow tube 2054. The diameter of the pin 2052 can be substantially the same as the inner diameter of the hollow tube 2054 or slightly smaller, such that the hollow tube 2054 can be translated along an axis corresponding to pin 2052 while the pin 2052 fills or occludes most or all of the inner lumen of the hollow tube 2054. The pin 2052 can be formed of a low-friction material, or coated with a low-friction material such as, e.g., Teflon® or the like, to facilitate motion of the hollow tube 2054 with respect to the pin 2052 and/or inhibit accumulation or sticking of biological material to the pin 2052. The distal end of the pin 2052 can be substantially flat to facilitate displacement of a tissue micrograft within the hollow tube 2054, when the hollow tube 2054 is translated relative to the pin 2052.

The hollow tube 2054 can be translated relative to the pin 2052, e.g., substantially along the longitudinal axis of the hollow tube 2054. In this manner, the position of the distal end of the hollow tube 2054 relative to that of the distal end of the pin 2052 can be controllably varied. For example, the location of the distal ends of both the hollow tube 2054 and the pin 2052 relative to that of the lower surface of the substrate 2058 can be controllably and independently selected and varied.

FIG. 6B shows one configuration of the present disclosure, in which the pin 2052 can be positioned relative to the hollow tube 2054 such that their distal ends are substantially aligned. In another configuration, the pin 2052 can extend slightly beyond the distal end of the hollow tube 2054, such that sharpened portions of the hollow tube 2054 can be shielded from undesired contact with objects and/or users. Portions of the pin 2052 and/or hollow tube 2054 can optionally be provided with a coating or surface treatment to reduce friction between them and/or between either component or biological tissue.

As described herein, a plurality of microneedles (e.g., microneedle 2050) can form a microneedle array 2006. FIG. 6C shows a top view of an exemplary microneedle array 2006, according to configurations of the present disclosure. In some configurations, the microneedle array 2006 can be substantially circular. The microneedle array 2006 can be formed by assembling a plurality of rows of needles, either horizontal or vertical rows. This design can be modular, and the configuration can take on any shape or size using various size rows as modules. In some configurations, all of the microneedles can be actuated, e.g., inserted into the tissue, simultaneously. In other configurations, groups or sections can be actuated sequentially. For example, the microneedle array 2006 can be divided into quadrants and each quadrant can be sequentially actuated. Sequentially can refer to actuating each row in a linear order, (e.g., row1, row2, row3), or non-linear (e.g. row1, row10, row3). Or, each row of microneedles can be separately and sequentially actuated. Additionally, each single microneedle can be separately and sequentially actuated. In some configurations, one row can be actuated at a time, e.g., 20 rows can be individually actuated in sequence, while in other configurations, two, three, four or more rows can be actuated at a time. An advantage to sequentially actuating segments of the microneedle array 2006 is that insertion of a segment can require less force on the donor site than insertion of the entire microneedle array 2006. In some configurations, the microneedle array 2006 can be driven using a solenoid (e.g., solenoid 1052). Multiple actuations using the solenoid can sequence the insertion row by row.

Figure 7:
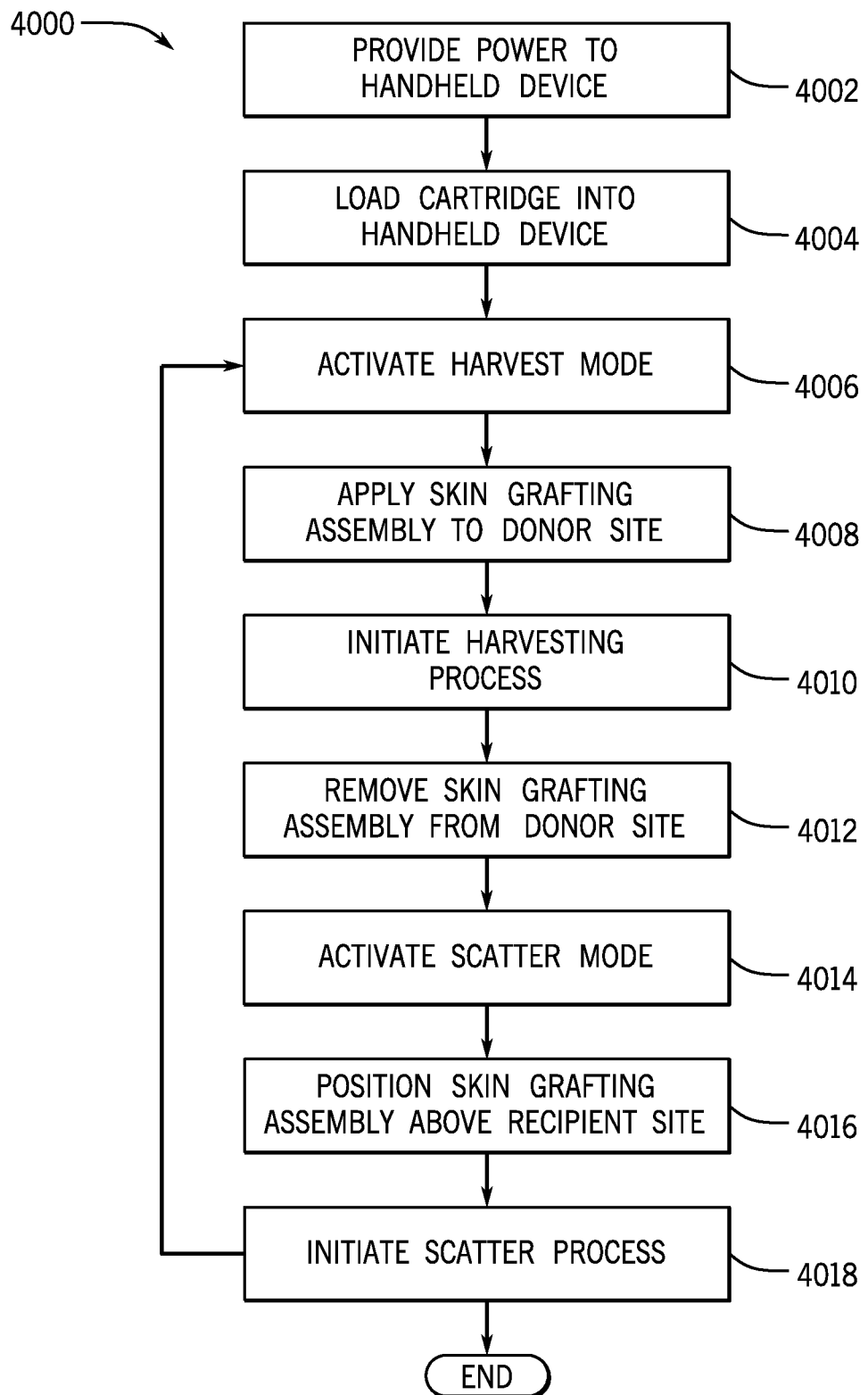
FIG. 7 is a procedural flowchart illustrating a method of harvesting and scattering tissue, in accordance with some implementations of the present disclosure.

Referring now to FIG. 7, some non-limiting examples of steps of a process 4000 for harvesting and scattering tissue is shown, according to configurations of the present disclosure. In some configurations, the process 4000 can be implemented using the skin grafting system 3000, as described above. As shown, the process 4000 includes providing power to the handheld device (process block 4002). In some configurations, the handheld device can be the same or similar to handheld device 1000. The process 4000 is shown to further include loading a cartridge into the handheld device (process block 4004). In some configurations, the cartridge can be the same or similar to cartridge 2002, or cartridge assembly 2000. Further, the process 4000 is shown to include activating a harvest mode (process block 4006). This activation can be initiated via user interface 1008, according to some configurations, such as will be described. Alternatively, the activation can be initiated via contact with a donor site. The process 4000 is shown to include applying a skin grafting system (e.g., skin grafting system 3000) to a donor site (process block 4008). The donor site can correspond to a healthy area of tissue on a patient. Next, the process 4000 is shown to include initiating a harvesting process (process block 4010). In some configurations, this initiation can occur via the above-described trigger 1014. The process 4000 is shown to further include removing the skin grafting system from the donor site (process block 4012). Next, the process 4000 is shown to include activating a scatter mode (process block 4014). In some configurations, this activation can occur via user interface 1008, such as will be described. The process 4000 is shown to further include positioning the skin grafting system above a recipient site (process block 4016). In some configurations, the recipient site can correspond to a damaged area of tissue on the patient. Next, the process 4000 is shown to include initiating a scatter process (process block 4018). In some configurations, this initiation can occur via actuation of the above-described trigger 1014. As shown, the process 4000 can end after the scatter process (process block 4018), or can return to process block 4006 to reactivate the harvest mode. In some configurations, a single cartridge (e.g., cartridge 2002) can be used multiple times on the same patient. Advantageously, if the recipient site is relatively large, multiple harvests and scatters can occur using a single cartridge. Accordingly, the process 4000 can continue with process blocks 4006 through 4018 until a user is ready to dispose of the cartridge.

According to configurations of the present disclosure, the harvest process and scatter process can be performed using skin grafting system 3000. A non-limiting description of the internal functions of the handheld device 1000 and cartridge 2002 are accordingly disclosed herein.

User Interface

Referring to FIG. 2B, as one non-limiting example, an example of using the user interface 1008 to control the above-described process is provided. Upon providing power to the handheld device, the stand-by input 1018 can flash green when the handheld device 1000 first powers on (e.g., for ~8 seconds at initial start-up). This can inform the user that the handheld device 1000 is performing a start-up self-test or other operation. As another non-limiting example, the stand-by input 1018 can produce steady green illumination when the handheld device 1000 is on and ready for subsequent use. In some configurations, pressing the stand-by input 1018 for a pre-determined amount of time (e.g., 3 seconds, 5 seconds, or the like) can cause the handheld device 1000 to enter a stand-by mode. Continuing with the non-limiting example, the stand-by input 1018 can stop producing light when the handheld device 1000 is in stand-by mode. Other light colors, patterns, and timing can be implemented, according to various configurations and preferences.

As another non-limiting example, the indicator light 1020 can produce steady white light when the handheld device 1000 is in harvest mode but sufficient pressure against a donor site has not been achieved, such as will be described during a skin grafting process. Further, the indicator light 1020 can produce steady green light when the handheld device 1000 is in harvest mode and sufficient pressure against the donor site has been achieved (and the trigger 1014 is disengaged). The indicator light 1020 can produce flashing green light when the handheld device 1000 is in the process of harvesting. If pressure drops below a threshold value during the harvesting process, the indicator light 1020 can produce flashing white light. Further, the indicator light 1020 can produce flashing white light when the handheld device 1000 is experiencing a fault condition.

In another non-limiting example, the scatter input 1022 can produce steady white light when the harvest process is complete. In some configurations, a subsequent press of the scatter input 1022 can cause the handheld device 1000 to enter a scatter mode. The scatter input 1022 can produce steady green light when the handheld device 1000 is in scatter mode. Similar to the indicator light 1020, the scatter input 1022 can produce flashing white light when the handheld device 1000 is experiencing a fault condition. In some configurations, the scatter input 1022 can produce flashing white light during the harvesting process, which can indicate that extraction recovery is needed. A subsequent press of the scatter input 1022 can activate an extraction recovery process. Once the extraction recovery process is complete, the scatter input 1022 can produce a steady white light. A detailed description of the extraction recovery process is provided below.

In some configurations, similar to the indicator light 1020, the indicator light 1016 can produce a solid green light when the handheld device 1000 is in the harvest mode and sufficient pressure against the donor site has been achieved (and the trigger 1014 is disengaged). Additionally, the indicator light 1020 can produce flashing green light during the harvesting process, according to some configurations.

Skin Grafting System Operating Positions

In some configurations, a plurality of operating positions corresponding to the skin grafting system 3000 can be defined. Notably, the skin grafting system 3000 can operate using additional operating positions not explicitly defined.

Some configurations of the present disclosure include a horizontal carriage home position, where the horizontal carriage assembly 1082 can be in a position that occludes the horizontal flag sensor 1064. This position can be a "safe" position that keeps the carriage away from other moving parts.

Some configurations of the present disclosure include a vertical carriage home position, corresponding to a calibrated position where the vertical carriage assembly 1108 can be aligned with the corresponding components for loading or for harvesting. This position can be below the vertical flag sensor occlusion point. From a user's perspective, it can appear that the vertical carriage assembly 1108 is closest to the engagement slot 1002 of the handheld device 1000.

Some configurations of the present disclosure include a vertical carriage unlock/scatter position corresponding to a calibrated position where the vertical carriage assembly 1108 has unlocked the needle retract slide 1110 by pushing the needle retract slide latches 1116a, 1116b over their respective unlock cams 1102a, 1102b. This can be the highest position the vertical carriage assembly 1108 will travel to. From a user's perspective, it can appear that the vertical carriage assembly 1108 is up inside the handheld device 1000.

Some configurations of the present disclosure include a "flipper in" position and a "flipper out" position. Each flipper 1074 can have two defined positions that the handheld device 1000 detects via flag sensors that can provide positive feedback that each position has been reached. The "flipper in," or retracted, position can correspond to when the flipper 1074 is safely away from moving parts. The "flipper out," or extended, position can correspond to when the flipper 1074 is blocking the top plate 1112. The "flipper out" position can be used for initialization, when the needle retract slide 1110 (and therefore the cartridge 2002) is locked.

Some configurations of the present disclosure include a vertical carriage lock position, corresponding to a calibrated position where the vertical carriage assembly 1108 can move to (with the flippers 1074 extended out) to compress the needle retract springs 1120 and to lock the needle retract slide latches 1116. This "locking" is what can allow the needles to later be retracted, while also locking the cartridge 2002 inside the handheld device 1000.

Some configurations of the present disclosure include a vertical carriage lock relax position, which can be a position that is offset from a calibrated lock position, where a properly locked needle retract slide top plate 1112 will no longer be putting pressure on the flippers 1074, and therefore the flippers 1074 can be safe to retract in. Conversely, if the needle retract slide top plate 1112 is not properly locked, this position can be designed to maintain enough pressure on the flippers 1074 so that they will not retract in. This position can enable the handheld device 1000 to positively sense a proper locking of the needle retract slide 1110.

Some configurations of the present disclosure include a vertical carriage extract position, which can be a position that is offset from a calibrated unlock position, where the needle retract slide 1110 will not be unlocked and the extended needles can be behind the tissue stabilizer 2014. After harvest, this position is where the vertical carriage assembly 1108 can go to extract the needles (containing the tissue grafts) from the tissue prior to scattering. Advantageously, tissue grafts may not be exposed in this position, as the needles remain extended.

Some configurations of the present disclosure include a harvest recovery mode, which can occur during the harvest process. The harvest recovery mode can include attempting to continue deploying the needle modules into the tissue. Additionally, the harvest recovery mode can be automatic and fully controlled by on-board software (i.e., no user interaction required). In some embodiments, the harvest recovery mode can include reversing the motion of the horizontal carriage assembly 1082 by a predetermined distance or time interval. Subsequently, the horizontal carriage assembly 1082 can advance and again attempt to deploy the needle modules into the tissue.

Some configurations of the present disclosure include an extraction recovery mode, which can occur after the needles have been deployed (and the handheld device 1000 is attempting to return the horizontal carriage to its home position). In some configurations, it may be possible for the horizontal carriage assembly 1082 to get stuck due to increased friction from the needle modules. If this occurs, the handheld device 1000 can blink the scatter light (on the scatter input 1022) white, indicating that an extraction recovery is needed. The user may then relieve the downward force on the tissue, and press the scatter input 1022, which will allow the handheld device 1000 to continue with extracting the needles from the tissue.

Skin Grafting Assembly Vertical Operation

Various components corresponding to the handheld device 1000 and cartridge 2002 can have a predefined operation based on the current mode of the handheld device 1000 (e.g., initialization, harvest mode, scatter mode, etc.), according to some configurations.

In some configurations, the vertical component assembly 1046 can have a predefined "loading" configuration that corresponds to loading of the cartridge 2002 into the handheld device 1000. During loading, for example, the solenoid plunger bar 1106, each flipper 1074, and the needle retract slide 1110 can be retracted (the needles retracted). The vertical carriage assembly 1108 can be set to the home position (as described above).

In some configurations, the vertical component assembly 1046 can have a predefined "initialization" configuration. During initialization, for example, each flipper 1074 can be extended (flipper out), and the needle retract slide 1110 can be locked with the needle retract springs 1120 loaded (the needles remain retracted). The vertical carriage assembly 1108 can be set to the lock position (see above). With each flipper 1074 extended, the vertical carriage assembly 1108 can move up to the lock position. The extended flippers 1074 can hold the needle retract slide 1110 in place. When the vertical carriage assembly 1108 reaches the lock position, the needle retract slide latches 1116 can lock the top plate 1112 in place with the needle retract springs 1120 loaded. In some configurations, this does not move the needles from their retracted state.

In some configurations, the vertical component assembly 1046 can have a predefined "initialized" configuration, which can correspond to the skin grafting system 3000 being ready to harvest. During the initialized configuration, for example, each flipper 1074 can be retracted (flipper in), and the needle retract slide 1110 can be locked with the needle retract springs 1120 loaded. In some configurations, this does not move the needles from their retracted state. The vertical carriage assembly 1108 can move back down to the home position, according to some configurations.

In some configurations, the vertical component assembly 1046 can have a predefined "harvest" configuration corresponding to an applied user force. During the harvest configuration, for example, the needle retract slide 1110 can remain locked with the needle retract springs 1120 loaded and the needles retracted. The vertical carriage assembly 1108 can remain in the harvest position, according to some configurations. When the user positions the skin grafting system 3000 at the donor site and applies downward force, the user will detect the tissue stabilizer 2014 moving a small amount in the direction opposite to the applied force, causing the indicator lights 1016 and 1020 to light up, indicating to the user that there exists proper alignment for harvest. In some configurations, the indicator light 1016 can illuminate green, to provide a visual confirmation of force to the user.

In some configurations, the vertical component assembly 1046 can have a predefined "harvest" configuration corresponding to needle deployment. During this harvest configuration, for example, the solenoid plunger bar 1106 can advance, and the needle retract slide 1110 can remain locked with the needle retract springs 1120 loaded. Notably, the needles (e.g., from microneedle array 2006) can be deployed into the tissue. The vertical carriage assembly 1108 can remain at the home position, and a user force can still be applied via the handheld device 1000, according to some configurations. When the user pulls the trigger 1014, the skin grafting assembly 3000 can begin the harvest sequence. Accordingly, the skin graft assembly 3000 can advance each microneedle array row of needles into the tissue by hitting the hammers 1098a, 1098b with the solenoid plunger bar 1106.

In some configurations, the vertical component assembly 1046 can have a predefined "extraction" configuration. During the extraction configuration, for example, the solenoid plunger bar 1106 can be retracted, the needle retract slide 1110 can remain locked with the needle retract springs 1120 loaded. The needles (e.g., from microneedle array 2006) can remain deployed into the tissue at the start of extraction. The vertical carriage assembly 1108 can move to the extraction position (described above). In some configurations, after the harvest is complete, the skin grafting system 3000 can extract the needles by lifting all of needles within the microneedle array 2006 at once. The needles can be lifted up to the extraction position, and the user force can be removed. In some configurations, the needles can remain advanced relative to the pins (e.g., pin 2052) and the tissue stabilizer 2014 can remain stationary when the needles are retracted.

In some configurations, the vertical component assembly 1046 can have a predefined "scatter" configuration. During the scatter configuration, for example, the needle retract slide 1110 can be in a retracted position, with the needles similarly retracted. In some configurations, the vertical carriage assembly 1108 can move from the extracted position. When the user activates the scatter sequence, the skin grafting system 3000 can move the vertical carriage assembly 1108 from the extracted position, which can release the loaded needle retract springs 1120, and the needle retract slide 1110. Accordingly, this movement can retract the needles relative to the pins (e.g., pin 2052), thus exposing the grafts and positioning the components for a scatter sequence.

In some configurations, the vertical component assembly 1046 can have a "scatter" configuration corresponding to an advanced needle position. During this scatter configuration, for example, the solenoid plunger bar 1106 can advance, and the needle retract slide 1110 can advance (similarly, the needles can advance). According to some configurations, the solenoid plunger bar 1106 can advance, first hitting the top plate 1112, and then hitting the needle modules (e.g., within microneedle array 2006). This can push the top plate 1112 ahead of needle carriers, thus preventing damage to the carriers. The advancing of the needles, followed by the rapid retraction of those needles (by the unlocked top plate 1112) can disperse the grafts into the recipient site.

Power on Self-Test

In some configurations, the handheld device 1000 can perform a self-test upon start-up (e.g., when the handheld device 1000 is first powered on). In some configurations, the self-test can occur when the handheld device 100 is plugged in to receive power, and the stand-by input 1018 is pressed and released. The stand-by input 1018 can flash green throughout the duration of the self-test, according to some configurations. Next, the horizontal carriage assembly 1082 can move a very small amount forward, such that the horizontal flag sensor 1064 is cleared. Subsequently, the horizontal carriage assembly 1082 can return to the home position.

During the self-test, the vertical carriage assembly 1108 can move a very small amount upwards, such that the vertical flag 1118 clears the sensor. Subsequently, the vertical carriage assembly 1108 can return to the home position. In some configurations, the vertical carriage assembly 1108 can move up to the unlock position, where it can move the needle retract slide latches 1116, before returning to the home position. This can, for example, release the needle retract slide 1110, in the event that it is locked (e.g., cartridge 2002 is locked in).

In some configurations, the horizontal carriage assembly 1082 can move to a predetermined position (e.g., approximately two-thirds of the way through its full range), which can verify that a cartridge (e.g., cartridge 2002) is not present. Subsequently, the horizontal carriage assembly 1082 can return to the home position.

During the self-test, the flippers 1074 can extend out and then retract back in. Further, in some configurations, some or all lights on handheld device 1000 can flash (e.g., indicator light 1016, 1020, scatter input 1022, etc.). Upon completion of the self-test, the stand-by input 1018 can light up solid green, for example, which can indicate that the self-test was successful.

Cartridge Loading and Initialization

In some configurations, the skin grafting system 3000 can have a predefined cartridge loading and initialization process. The user can open the loading door 1004, then slide the cartridge assembly 2000 (i.e., including the cartridge cover 2004) into the engagement slot 1002. The cartridge latch 1114 can lock onto the cartridge 2002. The user can then remove the cartridge cover 2004 and close the loading door 1004, which can activate the internal loading door switch.

The initialization process can further include moving the horizontal carriage assembly 1082 from the home position, such that it can detect the cartridge presence by stalling on the first cartridge segment. Subsequently, the horizontal carriage assembly 1082 can return to the home position. Additionally, the vertical carriage assembly 1108 can move a small amount, such that the vertical flag 1118 clears the sensor, and then the vertical carriage assembly 1108 can return to the home position.

In some configurations, the flippers 1074 can extend out above the top plate 1112. The vertical carriage assembly 1108 can move to the lock position. While moving to the lock position, the flippers 1074 can hold the top plate 1112 in place while the needle retract slide latches 1116 move out, and eventually lock over the top plate 1112. Accordingly, the needle retract springs 1120 can be held in a compressed state. While this is happening, for example, the lockdown latches 1126 can spring out under the needle segments (e.g., within the microneedle array 2006), in preparation for locking the needle segments down during the harvest sequence. In some configurations, the vertical carriage assembly can then move a small amount down, thus moving into the lock relax position (described above). Additionally, the flippers 1074 can retract back in.

The initialization process can further include returning the vertical carriage assembly 1108 to the harvest position. The horizontal carriage assembly 1082 can engage with the first needle segment (within microneedle array 2006) by stalling against the segment and subsequently backing off by a small predetermined distance. The handheld device 1000 can then calculate the position of each needle segment. Upon completion of the initialization process, the indicator light 1020 can illuminate white to indicate that the handheld device 1000 is ready for the harvest sequence.

Methods of Harvest and Extraction

In some configurations, a user can harvest and extract tissue columns using a harvesting process. The user can position the handheld device 1000 at the donor site, with the tissue stabilizer 2014 pressed against the skin. The user can use one or two hands to apply force against the skin via the handheld device 1000. The tissue stabilizer interface components can move upward, compressing the position sensing springs 1056 until the position sensing flag 1062 occludes the flag sensor. In some configurations, the indicator lights 1016, 1020 can illuminate green, thus indicating that the trigger 1014 is active.

Once the trigger 1014 is active, the user can pull the trigger 1014 (while maintaining the force on the skin) and the handheld device 1000 can begin the harvest sequence. In some configurations, the indicator lights 1016, 1020 can blink green throughout the duration of the harvest and the extraction. The position sensing flag 1062 can be monitored throughout the harvest (between solenoid activations) to ensure that sufficient force is maintained. The solenoid 1052 can rapidly advance the solenoid plunger bar 1106, which can advance the two hammers 1098a, 1098b, and insert the first needle module into the tissue. The needle module travels past the needle module lockdown latches as it is inserted. Subsequently, the solenoid 1052 and hammers 1098a, 1098b can retract, and the needle segment can remain locked down in the tissue.

In some configurations, the horizontal carriage assembly 1082 can advance to the calculated position of the next needle segment. Alternatively, the position of the next needle segment can be recalculated or otherwise re-verified throughout the harvest process. The solenoid 1052 can rapidly advance the solenoid plunger bar 1106, which can advance the two hammers 1098a, 1098b, and insert the next needle module into the tissue. The needle module can travel past the lockdown latches 1126 as it is inserted. The lockdown latches 1126 can spring back out, and the solenoid 1052 and hammers 1098a, 1098b can retract. This insertion process can repeat until all needle segments have been inserted into the tissue.

After completing the insertion of all segments, the horizontal carriage assembly 1082 can return to the home position, according to some configurations. The vertical carriage assembly 1108 can move up to the extraction position, extracting the needles from the tissue, and positioning the needles safely up inside the tissue stabilizer 2014. The indicator lights 1016, 1020 can stop blinking green and turn off. Additionally, the scatter input 1022 can be illuminated white, indicating that the handheld device 1000 is ready to proceed with the scattering process. Upon completion of the harvesting process, the user can remove the force on the tissue, and lift the handheld device 1000 away.

Methods of Scatter

In some configurations, a user can scatter the tissue columns after the harvesting process. Once the user has removed the handheld device 1000 from the donor site (with the tissue columns harvested), the needles can be safely up inside of the cartridge 2002 (e.g., within the tissue stabilizer 2014). With the recipient site ready for the tissue columns, the user can activate the scatter mode by pressing the scatter input 1022. In some configurations, the scatter input 1022 can change from being illuminated white to green.

In some configurations, the user can position the cartridge 2002 directly above the recipient site. The user can then pull the trigger 1014 and the vertical carriage assembly 1108 can move out of the extract position, which can release the needle retract slide 1110 and retract the needles behind the pins (e.g., pins 2052). The handheld device 1000 can rapidly advance the solenoid plunger bar 1106 which accordingly push both the needle retract slide 1110 and the needle modules. The needle retract slide 1110 can remain pushed ahead of the needle modules to prevent damage to the needle modules. Subsequently, the solenoid plunger bar 1106 can retract, which can cause the needle retract slide 1110 to retract (pulling the needle modules back with the needle retract slide 1110). The process of rapidly advancing the solenoid plunger bar 1106 can be repeated several times, which can ensure that as many grafts as possible have been deposited into the recipient site. In some configurations, six activations of the solenoid 1052 can occur. After the scatter process has completed, the vertical carriage assembly 1108 can return to the home position, with the needle retract slide 1110 unlocked.

Cartridge Removal

In some configurations, once the user has completed the harvest and scatter processes, the user can open the loading door 1004, depress the cartridge latch 1114, and slide the cartridge 2002 out. In some configurations, if the user wants to complete another harvest with the same cartridge 2002, the user can open and close the loading door 1004 (i.e., without removing the cartridge 2002). This can begin another initialization process via the handheld device 1000. Alternatively, the user can begin another initialization process via an input (not shown) on the user interface 1008.

Fluid Ingress Protection

As described above, the cartridge 2002 can be used for multiple harvest and scatter processes (on a single patient), before removal from the handheld device 1000 and subsequent disposal. In some situations, repeated tissue punctures via the microneedle array 2006 can cause localized bleeding. Further, the repeated deployment and retraction of the needle modules can result in the dispersion of blood or other fluids. Since the cartridge 2002 can be disposable, blood dispersion onto, for example, the exterior of the microneedle chamber 2018 may be inconsequential. However, the handheld device 1000 can be reusable. Accordingly, it may be advantageous to prevent blood ingress into housing 1036. As an example, should blood penetrate the housing 1036, an extensive cleaning and disinfecting process may be required.

The present disclosure includes systems and methods for preventing blood ingress. In particular, the present disclosure provides a device shield that can protect the contact point that occurs between the engagement slot 1002 and the cartridge 2002 (see, e.g., FIG. 1). Additionally, the device shield of the present disclosure can be designed to protect the contact point that occurs between the loading door 1004 and the cartridge 2002 (see, e.g., FIG. 1).

Figure 8:
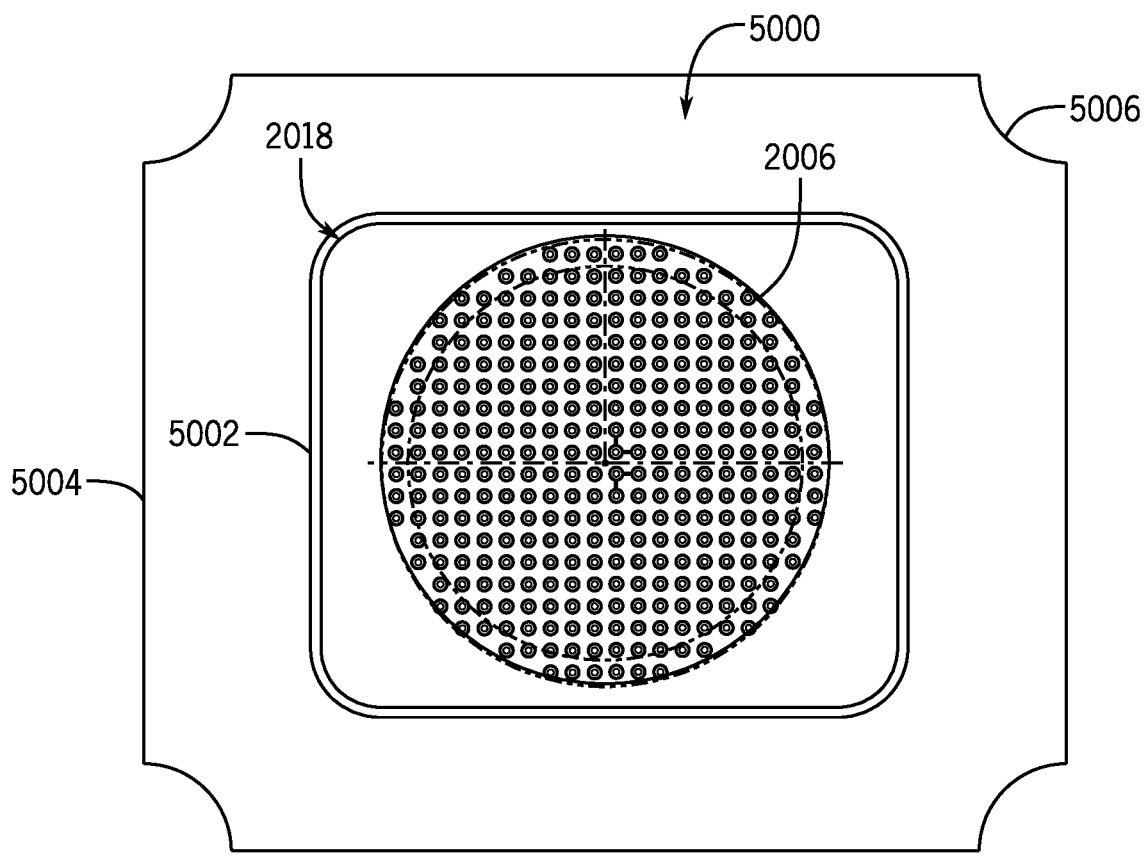
FIG. 8 is a front view of a device shield applied to a cartridge, in accordance with some implementations of the present disclosure.
Figure 9:
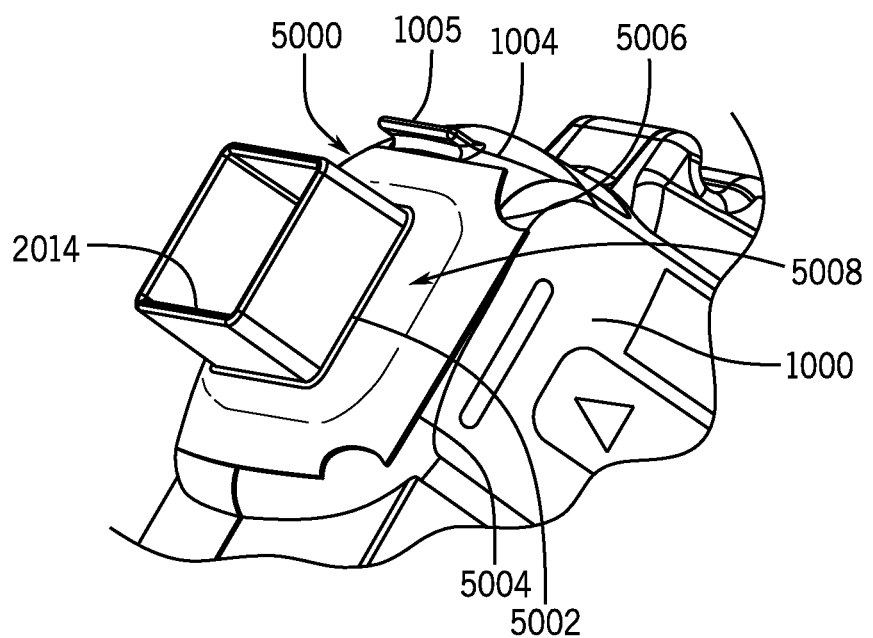
FIG. 9 is a perspective view of the device shield of FIG. 8, as applied to a skin grafting system, in accordance with some implementations of the present disclosure.

Referring now to FIGS. 8-9, a device shield 5000 is shown, according to configurations of the present disclosure. In general, the device shield 5000 can be configured to removably protect contact points between the cartridge 2002 and the handheld device 1000. The device shield 5000 is formed of a material (or multiple materials) that is impervious to liquid extending from an interior opening 5002 to an exterior edge 5004. At the exterior edge, corner cutouts 5006 may be included. Thus, as will be described, the device shield 5000 forms a barrier to fluids that surrounds or encircles the interior opening 5002.

The opening 5002 can engage the microneedle chamber 2018. In this way, when the cartridge 2002 is engaged with the handheld device 100, the device shield 5000 extends from the opening 5002 over the handheld device 1000 to the exterior edge 5004. In some configurations, a portion of the exterior edge 5004 can contact the loading door 1004 (see, e.g., FIG. 9). The loading door 1004 can optionally include a finger engagement 1005 (shown in FIG. 9), which can contact a portion of the exterior edge 5004. As shown, the finger engagement 1005 can extend past the device shield 5000 such that the loading door 1004 can be opened and closed even when the device shield 5000 is in place on the skin grafting assembly 3000.

In some configurations, the device shield 5000 can include corner cutouts (e.g., corner cutout 5006). As an example, the corner cutout 5006 can be inverted and/or rounded, such that a user can easily grasp the device shield 5000 during application and removal from the skin grafting assembly 3000.

In some configurations, the device shield 5000 can extend from an outer periphery of the tissue stabilizer 2014. The device shield 5000 inhibits blood flow onto and into the handheld device 1000, by, for example, protecting or sealing any openings corresponding to the engagement slot 1002 contact with the cartridge 2002, and the loading door 1004 contact with the cartridge 2002.

According to some configurations, the device shield 5000 can be formed of polymer that forms a barrier to fluids. Furthermore, the device shield 5000 may be formed of a pliable or an elastomeric material. The device shield 5000 may have a generally-flat geometry. By having a generally-flat geometry and being formed of a pliable or elastomeric material, the device shield opening 5002 can be dimensioned smaller than a perimeter dimension of the microneedle chamber 2018, such that the device shield 5000 can be stretched onto the microneedle chamber 2018. The stretching of the device shield 5000 can form a seal that is designed to be generally impenetrable to blood and other fluids impinging upon the device shield 5000, thus preventing fluid ingress into the handheld device 1000 along the tissue stabilizer 2014.

In the non-limiting example illustrated in FIG. 9, as the opening 5002 of the device shield 5000 is pulled down the tissue stabilizer 2014, the exterior edge 5004 can be pulled and, depending upon material selection and design, stretched away from the opening 5002, to extend toward the handheld device 1000. In this configuration, the device shield 5000 is no longer in the default, generally-flat geometry, but presents a slope or curve 5008 that extends from the opening 5002 to the exterior edge 5004.

The size of the device shield 5000 can vary, and in some embodiments, can be customized. As one example, the device shield 5000 can be cut to different shapes and sizes to customize the inhibition of blood ingress and usability of the skin grafting assembly 3000. According to some embodiments of the present disclosure, the device shield 5000 can be molded to a generally fixed shape and/or dimension. As one non-limiting example, the device shield 5000 can contact the exterior of the microneedle chamber 2018 (e.g., the tissue stabilizer 2014), and can otherwise extend outward therefrom (e.g., at a 90 degree angle, 45 degree angle, etc.). Accordingly, the device shield 5000 can provide a non-contact barrier for ingress points on the housing 1036.

Figure 10:
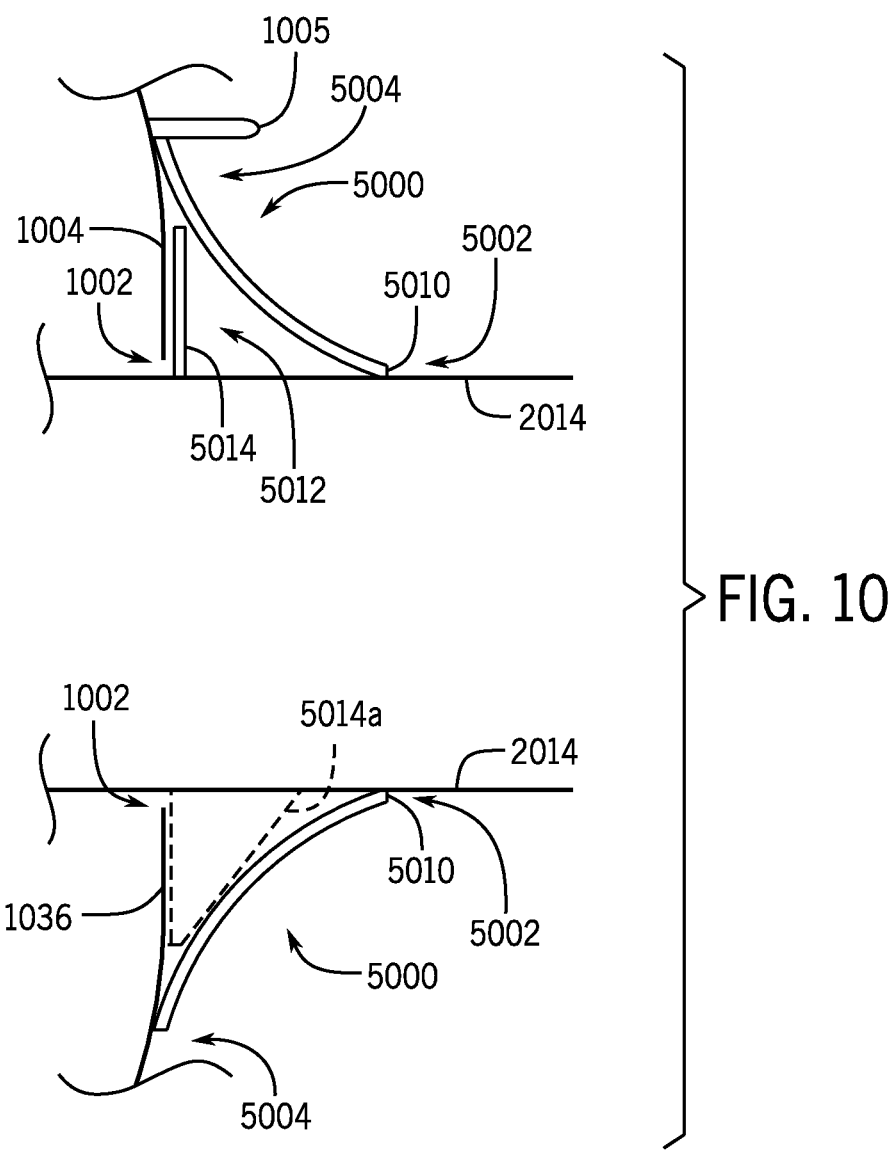
FIG. 10 is a cross-sectional view of the device shield of FIG. 8, as applied to a skin grafting system, in accordance with some implementations of the present disclosure.

Referring to FIG. 10, one non-limiting example of the device shield 5000 engaged with the tissue stabilizer 2014 and extending to loading door 1004 and housing 1036 is illustrated in vertical cross section. In this example, the device shield 5000 has an internal opening 5002 that is sized to be slightly smaller than or matched to the exterior of the tissue stabilizer. In this way, the device shield 5000 has been extended down over the tissue stabilizer 2014 by pulling on the exterior edge 5004, which stretches the device shield 5000 and, in this illustration, caused an interior surface 5010 of the device shield 5000 forming the interior opening 5002 when in a non-mounted position to extend perpendicular to the interior normal position and the tissue stabilizer. That is, because the interior opening 5002 is sized to carefully match the size of the tissue stabilizer 2014, the opening must stretch and deform to accommodate extension over the tissue stabilizer 2014, which causes the interior surface 5010 to be displaced to the illustrated, transverse position.

In some configurations, the device shield 5000 can be molded to provide a customized downward seal against the handheld device 1000 (and associated ingress points). As one non-limiting example, the device shield 5000 can be molded to align with a curvature of the tissue stabilizer 2014, the microneedle chamber 2018, and/or the loading door 1004. In the non-limiting example illustrated in FIG. 10, the device shield has assumed a concave orientation that forms a tight seal with the tissue stabilizer 2014 at the interior opening 5002 and the housing 1036 and loading door 1004 at the exterior edge 5004. Additionally, the device shield 5000 can be designed to provide a pocket 5012 between the device shield 5000 and the engagement slot 1002. The pocket 5012 can be configured to hold an absorbent material 5014 that can further inhibit blood ingress into the handheld device 1000. As illustrated, the absorbent material 5014 may be arranged as a ring or rectangle that engages and surrounds the tissue stabilizer 2014 and resides in the pocket 5012 over the engagement slot 1002. Alternatively, as illustrated in phantom, the absorbent material 5014*a* may have any of a variety of cross-sectional geometries or thicknesses.

While the present disclosure may be susceptible to various modifications and alternative forms, specific configurations have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the present disclosure as defined by the following appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this present disclosure.

The invention claimed is:

1. A skin grafting system comprising:
    a handheld device comprising a device housing forming an interior that secures a drive system;
    a cartridge comprising a plurality of hollow microneedles surrounded by a peripheral housing and configured to be operated by the drive system to extend and retract past the peripheral housing into a subject to harvest tissue during a skin grafting process; and
    a device shield formed of a polymer extending from an interior opening to an exterior edge, wherein the interior opening is sized to extend about the peripheral housing to position the exterior edge over the device housing to inhibit ingress of fluids into the interior of the device housing from fluid about the peripheral housing of the cartridge during the skin grafting process performed using the skin grafting system.

2. The system of claim 1 wherein the device shield is configured to form a barrier with the peripheral housing.

3. The system of claim 2 wherein the device shield is configured to deform to extend over the peripheral housing to form the barrier with the peripheral housing.

4. The system of claim 1 wherein the device housing forms an engagement slot to receive the cartridge and wherein the device shield is configured to extend over the engagement slot to arrange the exterior edge against the device housing to form a shield against fluid reaching the engagement slot.

5. The system of claim 4 wherein the device shield forms a pocket about the engagement slot.

6. The system of claim 5 further comprising an absorbent material arranged in the pocket.

7. The system of claim 6 wherein the absorbent material is configured to encircle the peripheral housing.

8. The system of claim 1 wherein the device shield is formed of an elastomeric material.

9. A skin grafting system comprising:
    a handheld device comprising a device housing having an engagement slot formed therein and creating an interior that secures a drive system;
    a cartridge that is removably engaged with the handheld device through the engagement slot and including a plurality of hollow microneedles surrounded by a peripheral housing and configured to be operated by the drive system to extend and retract past the peripheral housing into a subject to harvest tissue during a skin grafting process; and
    a device shield formed of a flexible membrane extending from an interior opening to an exterior edge, wherein the interior opening is sized to extend about and be moved along the peripheral housing to form a barrier over the engagement slot when the exterior edge is arranged to extend over the device housing.

10. The system of claim 9 wherein the device shield forms a seal with the peripheral housing.

11. The system of claim 10 wherein the device shield deforms to extend over the peripheral housing to form the seal with the peripheral housing.

12. The system of claim 9 wherein the device shield forms a pocket about the engagement slot.

13. The system of claim 12 further comprising an absorbent material arranged in the pocket.

14. The system of claim 13 wherein the absorbent material is configured to encircle the peripheral housing.

15. The system of claim 9 wherein the device shield is formed of a polymer that is impervious to liquid.

\* \* \* \* \*